Figure 2:
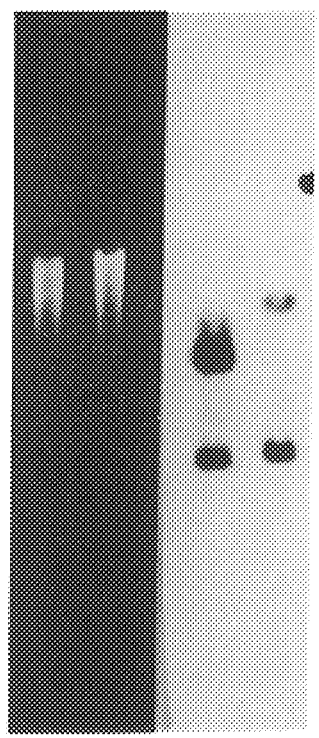

US005863728A

United States Patent [19]
Ho et al.

[11] Patent Number: 5,863,728
[45] Date of Patent: Jan. 26, 1999

[54] DNA ENCODING CARBOHYDRATE BINDING PROTEIN AND BIOLOGICAL MATERIALS DERIVED THEREFROM

[75] Inventors: John Siu-Cheong Ho, East Lansing, Mich.; John T. Loh, Knoxville, Tenn.; Melvin S. Schindler, Okemos; John L. Wang, East Lansing, both of Mich.

[73] Assignee: Board of Trustees operating Michigan State University, East Lansing, Mich.

[21] Appl. No.: 675,921

[22] Filed: Jul. 5, 1996

[51] Int. Cl.[6] ............................................ C12Q 1/68
[52] U.S. Cl. ........................ 435/6; 435/69.1; 435/91.2; 435/252.3; 435/320.1; 536/23.1; 536/24.3; 536/24.32
[58] Field of Search ................ 435/6, 69.1, 252.3, 435/320.1, 23.1, 24.3, 24.32, 91.2; 536/23.1, 24.3, 24.32

[56] References Cited

U.S. PATENT DOCUMENTS

| | | | |
|---|---|---|---|
| 4,713,330 | 12/1987 | McLoughlin | 435/34 |
| 4,782,022 | 11/1988 | Puhler et al. | 435/172.3 |
| 4,803,165 | 2/1989 | Appelbaum | 435/172.3 |
| 4,818,696 | 4/1989 | Appelbaum et al. | 435/172.3 |
| 4,863,866 | 9/1989 | Zablotowicz | 435/252.2 |
| 4,966,847 | 10/1990 | Stacey et al. | 435/172.3 |
| 4,983,519 | 1/1991 | Stacey et al. | 435/172.3 |
| 5,001,061 | 3/1991 | Rolfe et al. | 435/172.3 |
| 5,008,194 | 4/1991 | Rolfe et al. | 435/172.3 |
| 5,023,180 | 6/1991 | Appelbaum et al. | 435/172.3 |
| 5,045,461 | 9/1991 | Scott | 435/172.3 |
| 5,059,533 | 10/1991 | Watson et al. | 435/172.3 |
| 5,059,534 | 10/1991 | Appelbaum | 435/172.3 |
| 5,077,209 | 12/1991 | O'Gara | 435/172.3 |
| 5,124,260 | 6/1992 | Hauke et al. | 435/172.3 |
| 5,137,816 | 8/1992 | Rolfe et al. | 435/172.3 |
| 5,141,745 | 8/1992 | Rolfe et al. | 424/93 |
| 5,183,759 | 2/1993 | Triplett | 435/252.2 |
| 5,229,113 | 7/1993 | Kosslak et al. | 424/93 |

FOREIGN PATENT DOCUMENTS

0289947A1   9/1988   European Pat. Off. .

OTHER PUBLICATIONS

Nieuwkoop et al. (1987) J. Bact. vol. 169, pp. 2631–2638, 1987.
Nieuwkoop et al. (1988) GenBank database, Accession No. M16488, 1988.
Brewin, N.J., Ann. Rev. Cell Biol. 7:191–226 (1991).
Sanchez, F., et al., Ann. Rev. Plant Physiol. Mol. Biol. 42:507–528 (1991).
Fisher, R.F., et al., Nature 357:655–660 (1992).
Maxwell, C.A., et al., Plant Physiol. 93:1552–1558 (1990).
Long, S.R., Cell 56:203–214 (1989).
Lerouge, P., et al., Nature 344:781–784 (1990).
Spaink, H.P., et al., Nature 354:125–130 (1991).
Ehrhardt, D.W., et al., Science 256:998–1000 (1992).
Horvath, B., et al., Plant J. 4:727–733 (1993).
Truchet, G., et al., Nature 351:670–673 (1991).
Wang, J.L., et al., Trends Glycosci. Glycotech. 5:331–342 (1994).

Ho, S.C., et al., In: Lectin Reviews, (Kilpatrick, D.C., et al.,, eds.) vol. 1, pp. 171–181, Sigma, St. Louis, MO, USA (1991).
Dazzo, F.B., J. Supramol. Struct. Cell Biochem. 16:29–41 (1981).
Ho, S.C., et al., J. Cell Biol. 111:1639–1643 (1990).
Ho, S.C., et al., J. Cell Biol. 111:1631–1638 (1990).
Ho, S.C., et al., Plant Journal, 5:873–884 (1994).
Vesper, S.J., et al., Symbiosis 1:139–162 (1985).
Smith, G.B., et al., Can. J. Microbiol. 39:245–251 (1992).
Loh, J.T., et al., Proc. Natl. Acad. Sci 90:3033–3037 (1993).
Bhuvaneswari, T.V., et al., Plant Physiol. 66:1027–1031 (1980).
Calvert, H.E., et al., Can. J. Bot. 62:2375–2384 (1984).
Loh, J.T., et al., Glycoconjugate J., 11:363–370 (1994).
Peters, N.K., et al., Science 233:977–1008 (1986).
Zaat, S.A.J., et al., Plant Physiol. 86:1298–1303 (1988).
Kozzlak, R.M., et al., Proc. Natl. Acad. Sci. USA 84:7428–7432 (1987).
Mulligan, J.T., et al., Proc. Natl. Acad. Sci. USA 82:6609–6613 (1985).
Rossen, L., et al., EMBO J 4:3369–3373 (1985).
Banfalvi, Z., et al., Mol. Gen. Genet. 214:420–424 (1988).
Fisher, R.F., et al., Genes Dev. 2:282–293 (1988).
Hong, G.G., et al., Nucleic Acids Res. 15:9677–9690 (1987).
Gottfert, M., et al., Mol. Plant–Microbe Interact 5:257–265 (1992).
Jia, S., et al., Gene 60:197–204 (1987).
Carlson, T.A., et al., J. Bacteriol. 162:698–703.31 (1985).
Tumer, N.E., et al., Nature (Lond.) 306:337–341 (1983).
Adams, T.H., et al., J. Gen. Microbiol. 134:611–618 (1988).
Carlson, T.A., et al., J. Bacteriol. 169:5861–5866 (1987).
Smit, G., et al., J. Biol. Chem. 267:310–318 (1992).
Cangelosi, G.A., et al., Proc. Natl. Acad. Sci. USA 87:6708–6712 (1990).
Ankenbauer, R.G., et al., J. Bacteriol. 172:6442–6446 (1990).
Sanjuan, J., et al., Mol. Plant–Microbe Interact. 7:364–369 (1994).
Gottfert, M., et al., Proc. Natl. Acad. Sci. USA 87:2680–2684 (1990).
Hardy, R.W.F., et al., Soil Biol. Biochem. 5:47–81 (1973).
Stacey, G.S., et al., J. Bacteriol. 176:620–633 (1994).
Stacey, G., et al., Arch. Microbiol. 132:219–224 (1982).
Halverson, L.J., et al., Appl. Environ. Microbiol. 51:753–760 (1986).
Halverson, L.J., et al., Plant Physiol. 74:84–89 (1984).
Pierce, M., et al., Plant Physiol. 73:286–290 (1983).
Ridge, R.W., et al., J. Plant Physiol. 122:121–137 (1986).
Spaink, H.P., et al., In New Horizons in Nitrogen Fixation. Palacios R., Mora, J. Newton, W.E. pp. 165–170 (1993).

*Primary Examiner*—Robert A. Wax
*Assistant Examiner*—Enrique D. Longton
*Attorney, Agent, or Firm*—Ian C. McLeod

[57] ABSTRACT

A DNA fragment encoding a carbohydrate binding lectin BJ38 in chromosomal DNA of *Bradyrhizobium japonicum* is described. The DNA is used as a source of the lectin, as a probe and as DNA for recombinant strains of rhizobium with enhanced nodulation and production in legumes.

16 Claims, 9 Drawing Sheets

Experimentally determined peptide sequence:

V1– ▬▬
V2– ▬▬▬ – Thr Asn – Ala – Asp Gly – Thr – Asp Asn Leu Ala Ile – Ala Gln – Asn Ile →

V3– ─ ─
V4– ─ ─ ─ ← Val Val Phe Leu Val Thr Asp Gly Val Gly Asp Lys Ile Val Ser Gly Ala Ser

FIG. 1A

Deduced amino acid sequences from DNA sequence analyses:

Asp Asn Leu Ala Ile Arg Ala Gln Arg Asn Ile Thr Leu Arg Ile Asp ─────
───── (140 amino acids in an open reading frame of the nucleotide sequence) ─────
───── Thr Pro Gln Glu Val Val Phe Leu Val Thr Asp Gly Val Gly Asp Lys Ile

FIG. 1B

```
    cactgtcatcaaaccaatatcgctcacgacggcggaaccaaggatgacaacctcgcgatt
1   ------------+---------+---------+---------+---------+---------+  60
    gtgacagtagtttggttatagcgagtgctgccgccttggttcctactgttggagcgctaa ThrAsnIleAlaHisAspGlyGlyThrLysAspAspAsnLeuAlaIle cgcgcgcaaagaaatatcaccttgcggatcgatctcgcgaccgagtgccgtcgaccagtt
61  ------------+---------+---------+---------+---------+---------+
    gcgcgcgtttctttatagtggaacgcctagctagagcgctggctcacggcagctggtcaa ArgAlaGlnArgAsnIleThrLeuArgIleAspLeuAlaThrGluCysArgArgProVal gctgaaagtggtcgaactgcccgcagtcgggttttggggcggcgtcatgcagtgcatgtg
121 ------------+---------+---------+---------+---------+---------+
    cgactttcaccagcttgacgggcgtcagcccaaaacccgccgcagtacgtcacgtacac AlaGluSerGlyArgThrAlaArgSerArgValLeuGlyArgArgHisAlaValHisVal ggcgttgaaccaccaccacctacaaggggggcagtctatacgttcgatttgggtttcaacg
181 ------------+---------+---------+---------+---------+---------+
    ccgcaacttggtggtggtggatgttccccgtcagatatgcaagctaaacccaaagttgc GlyValGluProProProProThrArgGlyGlnSerIleArgSerIleTrpValSerThr actggccacactgaccaacccgaccagaaccaagcggcgggaaaccaggttcaacatcgc
241 ------------+---------+---------+---------+---------+---------+
    tgaccggtgtgactggttgggctggtcttggttcgccgccctttggtccaagttgtagcg ThrGlyHisThrAspGlnProAspGlnAsnGlnAlaAlaGlyAsnGlnValGlnHisArg gcttggaatggccggttcgcctaccagaattgcgtcggtgtgacgaccaactgcaaaacc
301 ------------+---------+---------+---------+---------+---------+
    cgaaccttaccggccaagcggatggtcttaacgcagccacactgctggttgacgttttgg AlaTrpAsnGlyArgPheAlaTyrGlnAsnCysValGlyValThrThrAsnCysLysThr
```

FIG. 7A

```
         gaaaatggcacagatatgccggcgcgcttaaaagcctcaacgacgttcatgcccaatccc
361      ---------+---------+---------+---------+---------+---------+
         cttttaccgtgtctatacggccgcgcgaattttcggagttgctgcaagtacgggttaggg GluAsnGlyThrAspMetProAlaArgLeuLysAlaSerThrThrPheMetProAsnPro gggcttgggagcaacgcgtcgggagatacgccgcaggaagtggtgttccttgtcaccgac
421      ---------+---------+---------+---------+---------+---------+
         cccgaaccctcgttgcgcagccctctatgcggcgtccttcaccacaaggaacagtggctg GlyLeuGlySerAsnAlaSerGlyAspThrProGlnGluValValPheLeuValThrAsp
                                                 ‾‾‾‾‾‾‾‾‾‾‾‾‾‾‾‾‾‾‾‾ ggcgtggaggacaagatcgtctcgggcgcttcgacttgccccaacgcgagcctcgcctcc
481      ---------+---------+---------+---------+---------+---------+
         ccgcacctcctgttctagcagagcccgcgaagctgaacggggttgcgctcggagcggagg GlyValGluAspLysIleValSerGlyAlaSerThrCysProAsnAlaSerLeuAlaSer
         ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾ aacaatcgatgccagcagccgctcgacacgacgatctgcacgaccatcaagaaccggggc
541      ---------+---------+---------+---------+---------+---------+
         ttgttagctacggtcgtcggcgagctgtgctgctagacgtgctggtagttcttggccccg AsnAsnArgCysGlnGlnProLeuAspThrThrIleCysThrThrIleLysAsnArgGly attaagatcgtgtcctctacacggaatacttgcaacttaagaccccaatatcccggtca
601      ---------+---------+---------+---------+---------+---------+
         taattctagcacaggagatgtgccttatgaacgttgaattctgggggttatagggccagt IleLysIleValSerSerThrArgAsnThrCysAsnLeuArgProProIleSerArgSer cgaacagctggtacatgctctgggtggacccgtacaacgcgcatacttccttgtccggga
661      ---------+---------+---------+---------+---------+---------+
         gcttgtcgaccatgtacgagacccacctgggcatgttgcgcggatgaaggaacaggccct ArgThrAlaGlyThrCysSerGlyTrpThrArgThrThrArgLeuLeuProCysProGly
```

FIG. 7B

```
        ccatcgcgcaaaaactgcaatcacgtcttcgcctggcttctatgcctccgtccaaaccgg
721     ---------+---------+---------+---------+---------+---------+ ggtagcgcgttttgacgttagtgcagaagcggaccgaagatacggaggcaggtttggcc

ProSerArgLysAsnCysAsnHisValPheAlaTrpLeuLeuCysLeuArgProAsnArg tggcgacatttccg
781     ---------+---- 794
        accgctgtaaaggc TrpArgHisPhe
```

FIG. 7C

DNA ENCODING CARBOHYDRATE BINDING PROTEIN AND BIOLOGICAL MATERIALS DERIVED THEREFROM

This invention was made with government support under Grant No. GM45200 by the National Institutes of Health. The government has certain rights in the invention.

BACKGROUND OF THE INVENTION (1) Summary of Invention

The present invention relates to isolated and purified DNA encoding a carbohydrate binding protein or lectin, designated as BJ38, which is a segment of chromosomal DNA of *Bradyrhizobium japonicum*. The DNA is used to provide the lectin, as a probe and as a basis for producing super nodulating strains of Rhizobium.

(2) Description of Related Art (2) Background and Rationale

Rhizobia encompass three genera of gram negative bacteria: Rhizobium, Bradyrhizobium and Azorhizobium (Brewin, N. J., Ann. Rev. Cell Biol. 7:191–226 (1991)). Each member of the three classes of rhizobia can nodulate a specific legume: *R. leguminosarum* bv. viciae nodulates pea and vetch; *R. leguminosarum* bv. trifolii (hereafter referred to as *R. trifolii*) nodulates clover; and *B. japonicum* nodulates soybean. This host specificity is observed throughout the nodulation process, including the early stages before infection initiation. It is most likely determined by multiple levels of interactions between components derived from both partners of the symbiosis (Erewin, N. J., Ann. Rev. Cell Biol. 7:191–226 (1991); Sanchez, F., et al., Ann. Rev. Plant Physiol. Mol. Biol. 42:507–528 (1991); and Fisher, R. F., et al., Nature 357:655:660 (1992)).

First, there are diffusible signals from the plant to the bacteria. Rhizobia are chemotactic towards specific flavonoid compounds released by the legume roots (Brewin, N. J., Ann. Rev. Cell Biol. 7:191–226 (1991); Sanchez, F., et al., Ann. Rev. Plant Physiol. Mol. Biol. 42:507–528 (1991); Fisher, R. F., et al., Nature 357:655:660 (1992); Maxwell, C. A., et al., Plant Physiol. 93:1552–1558 (1990)). The flavonoids induce transcription of an important set of nodulation (nod) genes in rhizobia. This process is mediated by nodD, the only nod gene constitutively expressed (Long, S. R., Cell 56:203–214 (1989)). NodD proteins from different species of rhizobia recognize different flavonoids preferentially and these activate the transcription of the other nod genes. Thus, this molecular recognition constitutes an important first level determinant of host-Rhizobium specificity (Brewin, N. J., Ann. Rev. Cell Biol. 7:191–226 (1991); Sanchez, F., et al., Ann. Rev. Plant Physiol. Mol. Biol. 42:507–528 (1991); Fisher, R. F., et al., Nature 357:655:660 (1992)).

Second, there are diffusible signals from the bacterium to the plant. The induction of bacterial nod genes results in the synthesis and secretion of Nod factors. Host specificity here is determined by species-specific chemical modification of the signal molecules. Nod factors secreted by *R. meliloti*, whose preferred host is alfalfa, and *R. leguminosarum* bv. viciae, which nodulates pea or vetch, are modified β-1,4-linked oligomers of N-acetyl-D-glucosamine (Lerouge, P., et al., Nature 344:781–784 (1990); and Spaink, H. P., et al., Nature 354:125–130 (1991)). The sulfate group of the *R. meliloti* factor is an important host specificity determinant (Ehrhardt, D. W., et al., Science 256: 998–1000 (1992) ), whereas the O-acetyl group and the nature of the fatty acyl substituent affect the biological activity of the *R. leguminosarum* bv. viciae factors (Spaink, H. P., et al., Nature 354:125–130 (1991)). The responses of plant cells to the Nod factors include membrane potential depolarization (Ehrhardt D. W., et al., Science 256:998–1000 (1992)), expression of genes specific for stages of infection and nodule organogenesis (the nodulins) (Horvath, B., et al., Plant J. 4:727–733 (1993)), and morphogenetic alterations such as curling of the root hairs (Truchet, G, et al., Nature 351:670–673 (1991)). The synthesis of the Nod factors is mediated by certain nod genes, which are under the transcriptional regulation of nodD protein (Brewin, N. J., Ann. Rev. Cell Biol. 7:191–226 (1991)).

The third level in determining host specificity occurs at the attachment of the rhizobia to the root surface (Wang, J. L., et al., Trends Glycosci. Glycotech. 5:331–342 (1994); Ho, S. C., et al., In: Lectin Reviews, (Kilpatrick, D. C., et al.,, eds.) Vol. 1, pp. 171–181, Sigma, St. Louis, MO, USA (1991); and Dazzo, F. B., J. Supramol. Struct. Cell Biochem. 16:29–41 (1981)). When the bacterial cells are inoculated on the seedling roots, they rapidly clump at the tips of the root hair cells. Over the course of several hours, the bacteria attach in a polar (end-to-end) fashion along the sides of the root hair. Within a few days, a marked curling of the root hair tip is induced and occasionally, bacteria entrapped within the curl penetrate the root hair cell wall to form a tubular structure called the "infection thread". The invading bacteria induce proliferation of cortical cells in the root, which eventually emerge as a nodule. These nodules contain bacteria that can reduce atmospheric nitrogen into ammonia, which is assimilated by the host plant.

Soybeans have vaulted into second place in value among all U.S. crops. They are surpassed only by corn. They outrank even corn as the single largest U.S. agricultural crop export. Soybeans are mainly used in two main products, meal and oil. They provide high quality human and animal foods as well as industrial products, including salad oil, high protein foods, like tofu, and a substitute for petroleum in industrial uses. The success of research directed agriculture is enlightening. Thanks to past research, national average yields have climbed from 23 bushels per acre in 1960 to about 37 at the present time. Researchers have even hit as many as 118 bushels per acre in maximum yield studies.

The attachment of *B. japonicum* to soybean root has been thoroughly analyzed (Wang, J. L., et al., Trends Glycosci. Glycotech. 5:331–342 (1993)). A galactose/lactose-specific bacterial lectin, namely BJ38 (mol. wt. 38,000) (Ho, S. C., et al., J. Cell Biol. 111:1639–1643 (1990) ) was identified and immunolocalized at one pole of the bacteria coincident with the point of attachment when the bacteria attached to the soybean root. This suggests a role for BJ38 in host recognition. Two binding deficient mutants showed no surface expression of BJ38 and significantly deficient in modulation activity (Ho, S. C., et al., J. Cell Biol. 111:1631–1638 (1990); and Ho, S. C., et al., Plant Journal, 5:873–884 (1994)). This established the importance of BJ38 for attachment and its involvement in nodulation. Further support of this idea comes from the strong correlation between three activities along the young root hair zone: bacterial attachment, activation of nod genes, and the susceptibility of the emergent root hair for nodulation.

In the Bradyrhizobium japonicum-soybean interaction, the attachment of bacteria to the host-legume is galactose (Gal)-specific (Vesper, S. J., et al., Symbiosis 1:139–162 (1985); Ho, S.-C., et al., J. Cell biol. 111:1631–1638 (1990); and Smith, G. B., et al., Can. J. Microbiol. 39:245–251 (1992)), suggesting the involvement of a carbohydrate-binding protein. Consistent with this observation, the isolation of the carbohydrate binding protein, BJ38, from *B. japonicum* was documented. BJ38 exhibits a saccharide specificity similar to that of bacterial adhesion to soybean roots (Ho, S.-C., et al., J. Cell biol. 111:1639–1643 (1990)). In addition the lectin has also been immunolocalized at the attachment site of bacterial attachment to soybean cells (Loh, J. T., et al., Proc. Natl. Acad. Sci. 90:3033–3037 (1993)). Purified BJ38 binds to soybean roots at sites coincident with *B. japonicum* attachment: namely, at the emergent root hair zones (Ho, S.-C., et al., Plant J. 5:873–884 (1994)). These regions had previously been demonstrated by Bauer and coworkers (Bhuvaneswari, T. V., et al., Plant Physiol. 66:1027–1031 (1980); and Calvert, H. E., et al., Can. J. Bot. 62:2375–2384 (1984)) to be the most susceptible to initiation of infection by *B. japonicum*. It has been reported that the expression of BJ38 can be induced by both lactose (Lac) and the isoflavonoid genistein (Loh, J. T., et al., Glycoconjugate J., 11:363–370 (1994)). As genistein is a potent inducer of the nod genes of *B. japonicum*, this latter result suggests the possibility that BJ38 may be a member of the nod gene family.

The nod genes comprise a set of key bacterial elements in the infection process and are transcribed in response to specific flavonoid compounds secreted from the host-plant (Peters, N. K., et al., Science 233:917–1008 (1986); Zaat, S. A. J., et al., Plant Physiol. 86:1298–1303 (1988); and Kosslak, R. M., et al., Proc. Natl. Acad. Sci. USA 84:7428–7432 (1987)). This requires the presence of the nodd gene product (Mulligan, J. T., et al., Proc. Natl. Acad. Sci. USA 82:6609–6613 (1985); Rossen, L., et al., EMBO J 4:3369–3373 (1985); and Banfalvi, Z., et al., Mol. Gen. Genet. 214:420–424 (1988)), which, in association with the appropriate flavonoids, binds to the nod box promoter sequence preceding the nod genes and activates the transcription of these genes (Fisher, R. F., et al., Genes Dev. 2:282–293 (1988); and Hong, G. G., et al., Nucleic Acids Res. 15:9677–9690 (1987)). In *B. japonicum*, two copies of nodd, $nodD_1$ and $noD_2$, have been identified (Gottfert, M., et al., Mol. Plant-Microbe Interact. 5:257–265 (1992)). Of these two nodD genes, only $nodD_1$ is both inducible by is of lavonoids and necessary for nod gene induction.

The patent art relating to Rhizobium is substantial and is exemplified by U.S. Pat. Nos. 4,713,330 to McLouchlin, 4,782,022 to Puhler et al, 4,803,165 to Appelbaum, 4,818,696 to Appelbaum et al, 4,863,866 to Zablotowicz, et al, 4,966,847 to Stacey et al, 4,983,519 to Stacey, et al, 5,001,061 to Rolfe et al, 5,008,194 to Rolfe et al, 5,023,180 to Appelbaum et al,5,045,461 to Scott, 5,059,533 to Watson et al,5,059,534 to Appelbaum, 5,077,209 to O'Gara, 5,124,260 to Hauke et al, 5,137,816 to Rolfe et al,5,141,745 to Rolfe et al,5,183,759 to Triplett, 5,229,113 to Kosslak et al, and European Patent Appln. 0 289 947A1.

There is a need to isolate super nodulating strains of *B. japonicum* for use as inoculants to enhance soybean crop yield based on their superiority in binding and infecting soybean root at the sites for nodulation and on the superiority in competitiveness against other indigenous Rhizobium strains which are inferior in nitrogen-fixing efficiency. There is also a need to isolate the DNA encoding BJ38.

OBJECTS

It is therefore an object of the present invention to provide DNA encoding lectin BJ38 which enables enhanced binding and nodulation by Bradyrhizobium japonicum in soybeans. Further, it is an object of the present invention to provide a source of the purified lectin BJ38 using recombinant DNA methods. Further, still it is an object to provide a probe for use in detecting DNA encoding the lectin BJ38. These and other objects will become increasingly apparent by reference to the following description and the drawings.

BRIEF DESCRIPTION OF DRAWINGS

FIGS. 1A shows the partial amino acid sequences of peptides derived from BJ38. BJ38 was digested with V8 protease, subjected to SDS-PAGE, transferred to a Problot membrane and Coomassie blue stained. Peptides were subjected to amino acid sequence analysis and the sequences for V2 and V4 (SEQ ID NOS:4 and 5) are shown at the right. The arrows highlight the amino acid sequences used to synthesize the 5'- and 3'-primers (direction indicated by the arrow) used for PCR amplification.

FIG. 1B shows the deduced amino acid sequences of fragments of PCR1 (SEQ ID NOS: 6 and 7). The underlined amino acid residues represent direct matches between the amino acid sequence deduced from the nucleotide sequence of the PCR product and the experimentally determined amino acid sequence from the protein of FIG. 1A.

FIG. 2 is a photograph of a Southern blot of *B. japonicum,* which has been digested with endonucleases that do not contain cleavage sites within the PCR1 probe. 3 μg of *B. japonicum* DNA was digested with 20 units of EcoRI, and BamHI and the digested DNA subjected to 0.8% agarose gel electrophoresis. DNA was transferred to Nytran membranes and the filters probed with $^{32}$P-labeled PCR1. Lanes a and c, EcoRI digestion; lanes b and d, BamHI digestion. Lanes a and b, ethidium bromide staining; lanes c and d, hybridization with $^{32}$-labeled PCR1.

FIG. 3A shows Northern blots of RNA that had been hybridized with $^{32}$P-labeled PCR1. RNA was isolated, subjected to 1 agarose gel electrophoresis and transferred to nitrocellulose membranes. The blots were then hybridized with the $^{32}$P-labeled PCR1, washed and analyzed by audioradiography. Lanes: a) *B. japonicum*; b) *R. meliloti;* and c) *R. trifolii* RNA.

FIG. 3B shows Northern blots of *B. japonicum* RNA that had been hybridized with: a) PCR1; b) $nodD_1$; c) glnA; d) galectin-3 probes.

FIGS. 4A and 4B are graphs showing the effect of flavonoids on the mRNA levels of BJ38 and $nodd_1$. Final liquid cultures were incubated for 10 hours in the presence of 2 μM concentrations of genistein, apigenin, luteolin or without any flavonoid treatment. The amount of each transcript is represented in intensity units. FIG. 4A) BJ38 transcripts; FIG. 4B) $nodD_1$ transcript.

FIGS. 5A and 5B are graphs showing the effect of saccharides on mRNA levels of BJ38 and $nodD_1$. Final liquid cultures of *B. japonicum* were incubated for 10 hours in the presence of 1 mM concentrations of Lactose (Lac), galactose (Gal), mannose (Man) and without any saccharide. FIG. 5A BJ38 transcripts. FIG. 5B $nodD_1$ transcript.

FIG. 6 is a chart showing a 7 kb segment contained in plasmid pBS-L3R2 as described in Example 2 and from which the DNA sequence of SEQ ID NO:1 and SEQ ID NO: 8 was derived.

FIGS. 7A to 7C are a DNA sequence encoding BJ38 (SEQ ID NO:1 and SEQ ID NO:8).

DESCRIPTION OF PREFERRED EMBODIMENTS

The present invention relates to DNA free of other DNA (particularly isolated and purified DNA) encoding a carbohydrate binding protein, designated as BJ38, the DNA being present in an EcoRI and BamHI segment of chromosomal DNA of *Bradyrhizobium japonicum*. The DNA can be recognized by a labeled DNA binding probe for the DNA.

The present invention relates to a recombinant plasmid containing DNA encoding a protein, designated as BJ38, the DNA being present in an EcoRI-BamHI segment of chromosomal DNA of derived from *Bradyrhizobium japonicum*.

The present invention relates to a *Bradyrhizobium japonicum* containing recombinant DNA encoding a carbohydrate binding protein, designated as BJ38, the DNA being present in a EcoRI and BamHI segment of chromosome DNA of *Bradyrhizobium japonicum*.

The present invention relates to a method of detecting MRNA encoding a protein, designated as BJ38, which comprises: binding the mRNA with a labeled DNA binding probe specific to the mRNA encoding the BJ38 under stringent conditions; and detecting the probe bound to the mRNA.

The present invention relates to a method of detecting a segment of DNA encoding a protein, designated as BJ38, which comprises: digesting DNA of *Bradyrhizobium japonicum* with endonucleases EcoRI and BamHI to produce the segment of the DNA which encodes a RNA for the BJ38; binding the segment of the DNA of the *Bradyrhizobium japonicum* with a labeled DNA probe which selectively binds the DNA on the segment; and detecting the labeled DNA probe bound to the segment of the DNA.

The present invention relates to a method for producing a cDNA encoding a carbohydrate binding protein, designated as BJ38, which comprises: binding oligonucleotide primers which are unique for DNA encoding the protein with DNA from *Bradyrhizobium japonicum*; amplifying the primed DNA by means of a polymerase chain reaction (PCR) to produce the cDNA; and isolating the cDNA.

The preferred strains are on deposit under the Budapest Treaty with the American Type Culture Collection, Manassas, Va. as ATCC 55749 (R110d) deposited on Mar. 27, 1996 and as ATCC 97494 (pBS-L3R2) deposited Mar. 27, 1996. The strains are available as required by the Budapest Treaty.

EXAMPLE 1

MATERIALS AND METHODS

Cell Cultures

*B. japonicum* cells (R110d) were maintained on YEG (yeast-extract-gluconate) agar plates for 3 days as described previously (Loh, J. T., et al., Glycoconjugate J., 11:363–370 (1994)). B. japonicum (R110d) was originally obtained from Dr. Barry Chelm of Michigan State University. This bacterial strain was maintained on agar plates containing yeast extract-sodium gluconate medium (YEG) and 50 mM lactose. YEG contained (per liter): 1.28 g $K_2PO_4$, 0.2 g $Mg_2SO_4 \cdot 7H_2O$, 7.35 mg $CaCl_2 \cdot 2H_2O$, 28 mg sequestrene, 5.0 g gluconic acid, and 1.0 g yeast extract, and was supplemented with trace elements: 2.5 mg $Na_2$ EDTA, 4.39 mg $ZnSO_4 \cdot 7H_2O$, 0.77 mg $MnSO_4 \cdot H_2O$, 0.15 mg $CuSO_4 \cdot 5H_2O$, 2.49 mg $Na_2MoO_4 \cdot 2H_2O$, 0.23 mg $CoCl_2 \cdot 6H_2O$, 0.46 mg $Na_2B_4O_7 \cdot 10H_2O$, 0.38 mg $Na_3VO_4$, and 0.1 mg $NaSeO_3$, pH 6.0. The bacteria (3-day-old) were transferred from the agar plate to 50 ml YEG in a 125 ml Erlenmeyer flask and cultured for one day. The bacterial suspension was then inoculated into 2 liters of YEG and cultured for 2 days on a gyratory shaker (120 rpm) at 30° C. Aliquots of this culture (300 ml) were then inoculated into six Fernbach flasks, each containing 1.5 liters of YEG. The bacteria were further cultured for about 30 hours until a value of 1.7–2.0 was obtained for the absorbance at 620 nm ($A_{620}$). The bacterial cells were then inoculated into 50 ml YEG and cultured in a gyratory shaker for 2 days. This culture was then transferred to 2 liter of YEG and grown for 2 more days. Aliquots of 300 ml of the 2 liter bacterial cultures were then transferred to 1.5 liter YEG to obtain the final liquid culture step. On the initiation of the final liquid culture, saccharides and flavones were added to a final concentration of 1 mM, and 2 $\mu$M, respectively and the bacteria cells were cultured for 10 hours prior to analysis. Lactose (Lac) was obtained from Kodak (Rochester, New York); mannose, genistein, apigenin, naringenin from Sigma (St. Louis, MO). Luteolin was kindly provided by Dr. Franz De Bruijn (Michigan State University).

The *R. meliloti* 1021 and *R. leguminosarum* bv. trifolii (*R. trifolii*) ANU843 strains were maintained on agar plates containing Minimum Bergensens Media III (MBM) (Dazzo, F. B., In Experimental Microbial Ecology. R. Burns, and T. Slater, editors. Blackwell Scientific Publications, Oxford, U. K. pp431–446 (1982)). Liquid cultures of these strains were initiated by inoculation of the bacterial cells (2 day old, MBM agar plates) into 50 ml MBM. The bacterial cells were grown for 12 hours at 30° C. before being transferred to 1 liter of MBM. This final 1 liter culture was then allowed to grow for 10 hours.

Determination of the Partial Amino Acid Sequence of BJ38

Purified BJ38 (12 $\mu$g) was digested with Staphylococcus aureus V-8 protease (Miles Laboratories, Naperville, Ill.) as described by Cleveland et al (Cleveland, D. W., et al., J. Biol. Chem. 252:1102–1106.20 (1977)). The digestion was carried out with 0.6 $\mu$g of enzyme for 0.5 hours. The peptides generated were subjected to SDS-PAGE electrophoresis (Laemmli, U. K., Nature (Lond.) 227:680–685 (1970)), transferred to a problot membrane (Applied Biosystems, Foster City, Calif.) and the digestion products revealed by Coomassie blue staining. Amino acid sequencing was performed by the Edman degradation method (Edman, P., et al., Eur. J. Biochem. 1:80–91 (1967)) on a Model 477A Gas Phase Sequencer (Macromolecular Structure Facility, Michigan State University, East Lansing, Mich.).

Polymerase Chain Reaction (PCR) Amplification and Nucleotide Sequence of PCR products Using the partial amino acid sequences obtained from BJ38, degenerate oligonucleotide primers were synthesized based on the codon usage in *B. japonicum*. PCR amplification was performed, with *B. japonicum* genomic DNA as a template, on an Automated DNA Thermal Cycler 9600 (Perkin Elmer Cetus, Norwalk, Conn.) using the protocol described by Saiki (Saiki, R. K., et al., Amplification of genomic DNA. In PCR protocols: A guide to methods and applications. M. A. Innis, D. H. Gelfand, and J. J. Sninsky, editors. Academic Press, Inc., San Diego, Calif. pp. 13–20 (1990)). The procedure consists of a denaturing step (94° C., 2 min) followed by 35 amplification cycles of denaturation (94° C., 1 min), annealing (55° C., 1 min) and extension (72° C., 2 min). For BJ38 amplification, 5 additional cycles (denaturation (94° C., 1 min), annealing (37° C., 5 min) and extension (72° C., 2 min) were included prior to the 35 amplification cycles. Following amplification, further extension at 72° C. (5 min) was allowed before cooling to 4° C. PCR products were then isolated using a QIAGEN DNA isolation kit (QIAGEN Inc., Chatsworth, Calif.) and eluted with 20 $\mu$l of 10 mM Tris, 0.1 mM EDTA, pH 8.0.

DNA sequencing was performed by the dideoxy chain termination method of Sanger et al (Sanger, F., et al., Proc.

Natl. Acad. Sci. USA 74:5463–5467 (1977)) using the pBluescript II SK (+) phagemid (Stratagene, San Diego, Calif.). For subcloning of PCR derived DNA fragments into the pBluescript vector, the phagemid was first digested with EcoRV (Boerhinger Mannheim Biochemicals, Indianapolis, Ind.). Addition of T's to the blunt ends of the vector was then carried out using Taq DNA Polymerase and dTTP (Kovalic, D., et al., Nucl. Acids. Res. 19:4560 (1991); and Marchuk, D. M., et al., Nucl. Acids Res. 19:1154 (1991)). PCR fragments were then annealed to the phagemid utilizing the property that PCR products synthesized by Taq DNA polymerase result in the addition of single non-templated A's to the 3' ends of the duplex DNA strands. Sequencing was carried out using the Taquence kit Version 2.0 (U.S. Biochemical Corp., Cleveland, Ohio) and $^{35}$S-dATP (Dupont, NEN; 10 mCi/ml) according to the manufacturers instructions.

RNA Isolation and Northern Blot Analysis

For the extraction of mRNA, the bacterial cells were harvested by centrifugation in a GS3 rotor (11,000 g, 15 min) The pelleted cells were resuspended in 20 mM sodium acetate (pH 5.5), 1 mM EDTA, 10 mM β-mercaptoethanol, 10 mM sodium dodecyl sulfate (SDS). The suspension was immediately placed in a 65° C. water bath and an equal volume of hot phenol (65° C.) that had been equilibrated with 20 mM sodium acetate (pH 5.5) was added. After 5 min, the suspension was subjected to centrifugation (30,000 g, 20 min) in an SS-34 rotor at 4° C. to remove DNA and protein debris. The supernatant was extracted three times with phenol-chloroform (1:1), once with chloroform and precipitated by addition of 2.5 volumes of ethanol and 0.1 volume of 3M sodium acetate (pH 5.5). The RNA was washed with 800 ethanol, dried and resuspended in water.

Total RNA (20 μg) was subjected to gel electrophoresis in 1% agarose-formamide denaturing gels in 20 mM MOPS, 5 mM sodium acetate (pH 7.0), 10 mM EDTA, and transferred to nitrocellulose membranes (Schleicher and Schuell, Keene, N.H.) by capillary transfer (Maniatis, T., et al., In Molecular cloning: a laboratory manual. N. Ford, M. Ferguson, and C. Nolan, Editors. Cold Spring Harbor press, Cold Spring Harbor, N.Y. (1982)). The filters were blocked in hybridization buffer (50% formamide, 5X SSPE (1X SSPE is 150 mM NaCl, 10 mM sodium phosphate, 1 mM EDTA), 0.1% SDS, 100 μg/ml denatured salmon sperm DNA, 5X Denhardt's solution) for 1 hour. The composition of 5X Denhardt's solution was 0.1% bovine serum albumin, 0.1% polyvinylpyrrolidone, and 0.1 Ficoll in H$_2$O. DNA probes were labeled with [α-$^{32}$P] dCTP (Dupont, NEN, 10 mCi/ml) using random oligodeoxynucleotide primer labeling (Feinberg, A. P. and B. Vogelstein., Anal. Biochem. 132:6 (1983)), and were used at 10$^6$ cpm/ml. The filters were incubated for 24 hours at 42° C. The blots were washed three times with 2X SSPE, 0.1% SDS (15 min. each), and once in 0.1X SSPE, 0.1% SDS (1 h). The washed filters were exposed to Kodak X-Omat AR film with an intensifying screen at −80° C. The intensities of the bands were determined by scanning densitometric analysis with a Visage 110 densitometer (Bioimage Prod. Ann Arbor, Mich.).

Southern Blot Analyses

Genomic DNA was isolated by the standard phenol-chloroform method (Zyskind, J. W., et al., In Recombinant DNA Laboratory Manual. Academic Press, Inc., San Diego, Calif. pp. 12–13 (1992)). The DNA (3 μg) was then digested with 20 units of EcoRI and BamHI (Boerhinger Mannheim Biochemicals, Indianapolis, Ind.) using reaction conditions suggested by the manufacturer. The digested DNA was electrophoresed on 0.8% agarose gels, and transferred to nytran membranes (Schleicher and Schuell, Keene, N.H.). The filters were then blocked in hybridization buffer and hybridized with $^{32}$P-labeled probes as described for the Northern blot analyses. The filters were then washed twice in 2X SSC (1X SSC=0.15 M NaCl and 0.5M sodium citrate) and 0.1% SDS at 42° C. for 15 min. each, and once in 0.1X SSC and 0.1% SDS for 15 minutes at 42° C. before being exposed to Kodak X-Omat AR film.

nodD$_1$, glnA, galectin-3 Oligonucleotide Probes

The nodD$_1$, probe was obtained by PCR amplification of the B. japonicum genomic DNA using the sequences -(dATCTAAATCTTCTCGTTGCGCTC)—SEQ ID NO:2 and —(dCGAGCAATATCCGACGCATCCAGA)—SEQ ID NO:3 complementary to the 5' and 3' ends of the published nodD$_1$ sequence (Gottfert, M., t al., Mol. Plant-Microbe Interact. 5:257–265 (1992)), respectively. A PCR product of 870 bp was obtained whose size was as expected from the sequence. In addition, a 270 bp stretch of the PCR product was sequenced and this segment demonstrated 100% identity to the reported nodD$_1$ sequence (Gottfert, M., et al., Mol. Plant-Microbe Interact. 5:257–265 (1992)). The cDNA of galectin-3 from mouse 3T3 cells was as described in Jia et al (Jia, S., et al., Gene 60:197–204 (1987)).

The glutamine synthetase probe (glna) was in the form of the plasmid pBJ53 (Carlson, T. A., et al., J. Bacteriol. 162:698–703.31 (1985)). The plasmid was digested with EcoRI and BglII to liberate a 0.8 kb fragment from within the coding sequence, as expected from restriction map analyses. This 0.8 kb glnA fragment was chosen as the glutamine synthetase probe in Northern blot analyses.

RESULTS

A Molecular Probe for the BJ38 gene(s)

Coomassie blue staining of purified BJ38, that had been digested with V-8 protease and subjected to SDS-PAGE, identified four peptides: Vi (38 kd), V2 (31 kd), V3 (21 kd) and V4 (14 kd). Amino acid sequence analyses of V2 and V4 yielded partial amino acid sequences as indicated in FIG. 1A, SEQ ID NOS: 4 and 5. No sequence was obtained from V1 and V3. Two degenerate primers (a sense oligonucleotide primer derived from V2 and an anti-sense primer derived from V4) were synthesized on the basis of their partial amino acid sequences and codon usage. Using genomic DNA isolated from B. japonicum as a template for PCR amplification, a DNA fragment (designated PCR1) of about 0.45 kb was obtained. The PCR fragment was sequenced and the deduced amino acid sequence of the PCR fragment matched exactly the experimentally determined amino acid sequence, both at the ends corresponding to the PCR primers, as well as internal regions not specified by the primers (FIG. 1B)—SEQ ID NOS: 6 and 7). PCR1 was thus used as an authentic probe for the BJ38 gene.

Southern and Northern Blot Analysis using the BJ38 probe

In these experiments, chromosomal DNA was first digested with the restriction endonucleases EcoRI and BamHI. These enzymes were chosen because they do not possess cleavage sites within the PCR1 probe. Southern blot analysis of the digested genomic DNA samples probed with PCR1 revealed, in each case, two bands (FIG. 2). These results suggest the possibility that there are either two genes for BJ38, or the presence of another gene, besides the BJ38 gene, that can hybridize with the PCR1 probe.

Figures 3A, 3B:
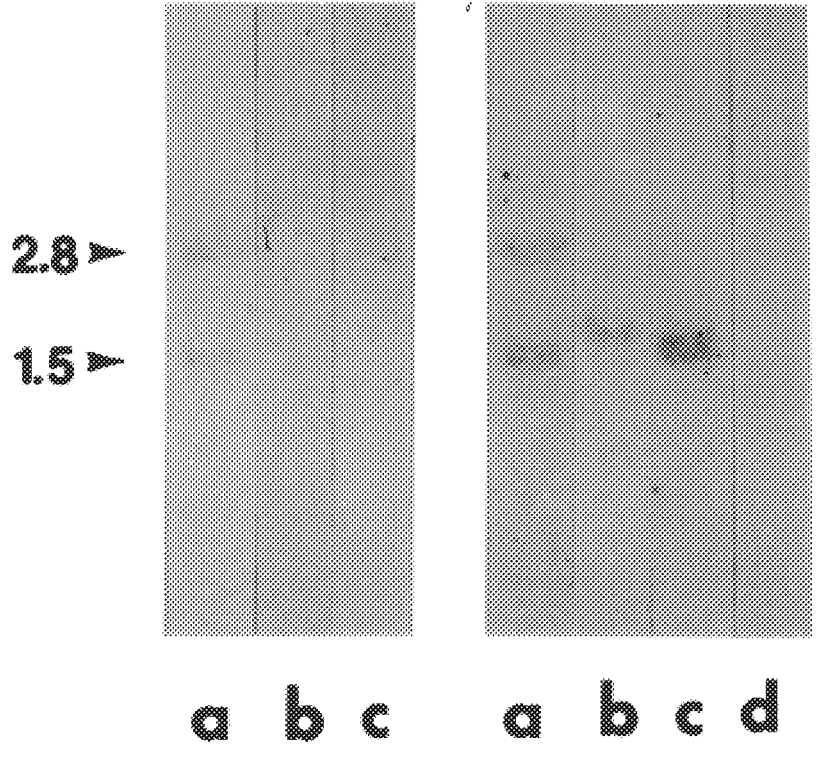

When Northern blots of B. japonicum RNA were probed with PCR1, the BJ38 probe hybridized to 2 bands of 1.5 kb and 2.8 kb (FIG. 3A, lane a). As a control, PCR1 was also used to probe RNA isolated from *R. meliloti* and *R. trifolii*, two rhizobial strains that do not bind to soybean roots. In both of these strains, no hybridization of PCR1 was observed (FIG. 3A, lanes b, c). When the $nodD_1$ probe was used to hybridize *B. japonicum* RNA, a single mRNA species of 1.6 kb was observed (FIG. 3B, lane b). The glutamine synthetase probe revealed a single band of ~1.5 kb as expected from the glna transcript (FIG. 3B, lane c) (Carlson, T. A., et al, J. Bacteriol. 162:698–703.31 (1985); and Tumer, N. E., et al., nature (Lond.) 306:337–341 (1983)). As a negative control, the cDNA of galectin-3 from mouse 3T3 cells were used to probe the RNA blots (Jia, S., et al., Gene 60:197–204 (1987)). As expected, this probe showed no hybridization to *B. japonicum* RNA (FIG. 3B, lane d).

The fact that the PCR1 probe hybridizes to two bands in both Southern and Northern blots suggests that there may indeed be two genes, each with its own distinct transcript. It is not clear whether the two mRNA species observed on the Northern blots are derived from one or distinct genes. In light of this result, the effects of saccharide and flavones on BJ38 expression are described in terms of both the two mRNA transcripts, hereafter, the 1.5 kb and 2.8 kb species are designated as transcript I and transcript II, respectively.

Effect of flavonoids on BJ38 and $nodD_1$ expression

BJ38 expression, assayed at the polypeptide level, was induced by the flavonoid genistein, a known nod gene inducer in *B. japonicum*. This raised the possibility that BJ38 may itself be a nod gene. Thus the effects of flavonoids on the accumulation of mRNA for BJ38 and $nodD_1$ were tested. In these experiments, RNA was isolated from liquid cultures of *B. japonicum* that had been exposed to 2 $\mu$M concentrations of flavones for 10 hours. This concentration of flavonoids was the same as were reported for genistein induction of BJ38 polypeptide (Loh, J. T., et al., Glycoconjugate J., 11:363–370 (1994)). Similarly, a 10 hour exposure to flavonoids had previously been shown to be sufficient for nod gene induction (Kosslak, R. M., et al., Proc. Natl. Acad. Sci. USA 84:7428–7432 (1987)). Finally, the transcript for the constitutively expressed glutamine synthetase (glna) gene (Adams, T. H., et al., J. Gen. Microbiol. 134:611–618 (1988); and Carlson, T. A., et al., J. Bacteriol. 169:5961–5866 (1987)) was used as an internal control in Northern blot analyses, as it had been previously shown that the level of glutamine synthetase enzymatic activity was unaffected by treatment with flavonoids (Loh, J. T., et al., Glycoconjugate J., 11:363–370 (1994)). Consistent with this previous study, the glnA transcript levels were not altered by the addition of flavonoids.

Figure 4A:
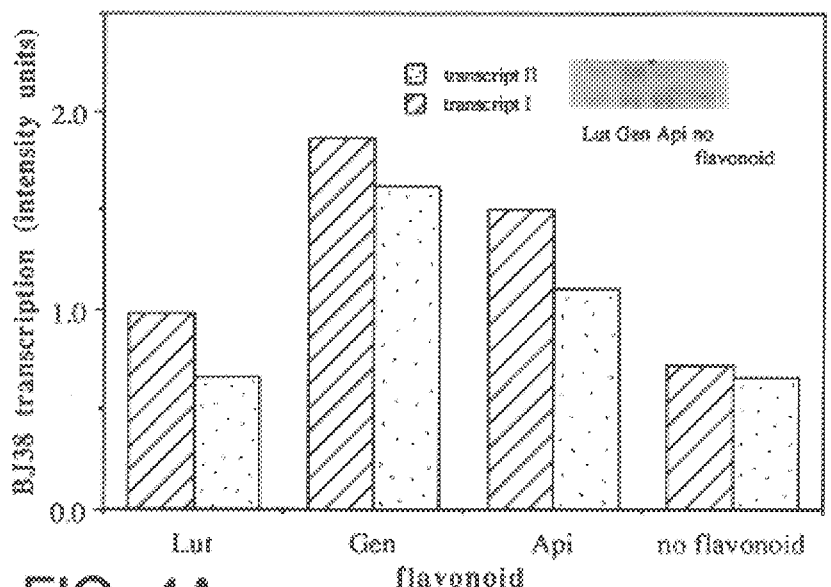
Figure 4B:
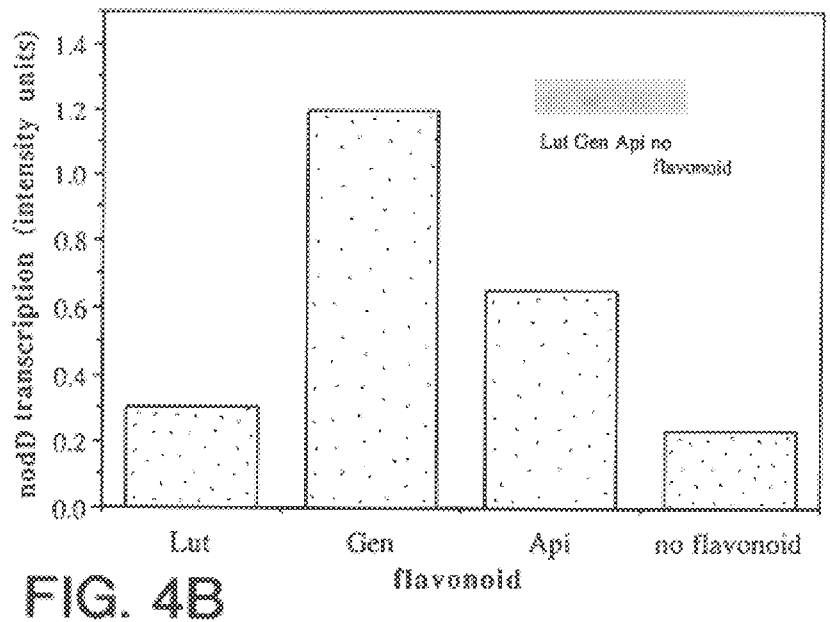

When RNA from B. japonicum was probed with PCR1, the BJ38 probe hybridized to two bands of 1.5 (transcript I) and 2.8 kb (transcript II) in both the untreated and flavonoid treated samples. The order of flavonoid induction for both transcript I and II was similar to that reported at the protein level, with genistein yielding the greatest effect (FIG. 4A). Luteolin yielded little or no effect, while apigenin yielded intermediate effects on BJ38 expression. In parallel, an examination of $nodD_1$ expression revealed that the $nodD_1$ gene was similarly induced by flavonoids. Genistein yielded the greatest effect, followed by apigenin (FIG. 4B). Luteolin failed to have an effect on $nodD_1$ mRNA levels. These latter results are consistent with previously reported effects on $nodD_1$ expression (Kosslak, R. M., et al., proc. Natl. Acad. Sci. USA 84:7428–7432 (1987); and Banfalvi, Z., et al., Mol. Gen. Genet. 214:420–424 (1988)).

Effect of saccharides on the expression of BJ38 and nod1.

It was shown that when *B. japonicum* cells were cultured in the presence of saccharides, the amount of BJ38 isolated from these cells was elevated in an order similar to the relative affinities of the saccharides for BJ38 (Loh, J. T., et al., Glycoconjugate J. 11:363–370 (1994)). Using the same protocol for flavone induction, the effects of saccharides on the accumulation of mRNA for BJ38 and $nodD_1$ were tested. Saccharides were added to a concentration of 1 mM and the cells cultured for 10 hours. This 10 hour length of exposure to Lac was selected as it had previously been shown to result in a 4–5 fold increase in the amount of BJ38 isolated from *B. japonicum* (Loh, J. T., et al., Glycoconjugate J., 11:363–370 (1994)). Consistent with the previous report, the glnA mRNA levels were unaffected by treatment of *B. japonicum* with saccharide.

Figure 5A:
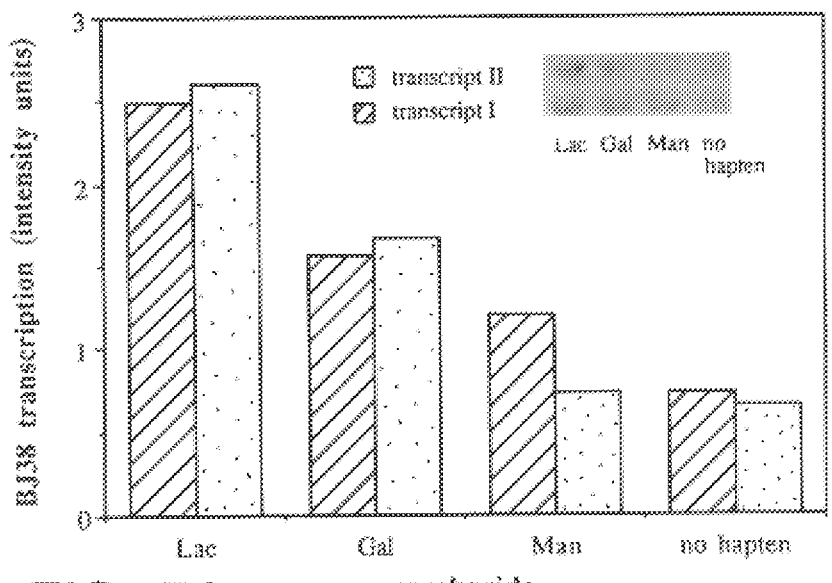
Figure 5B:
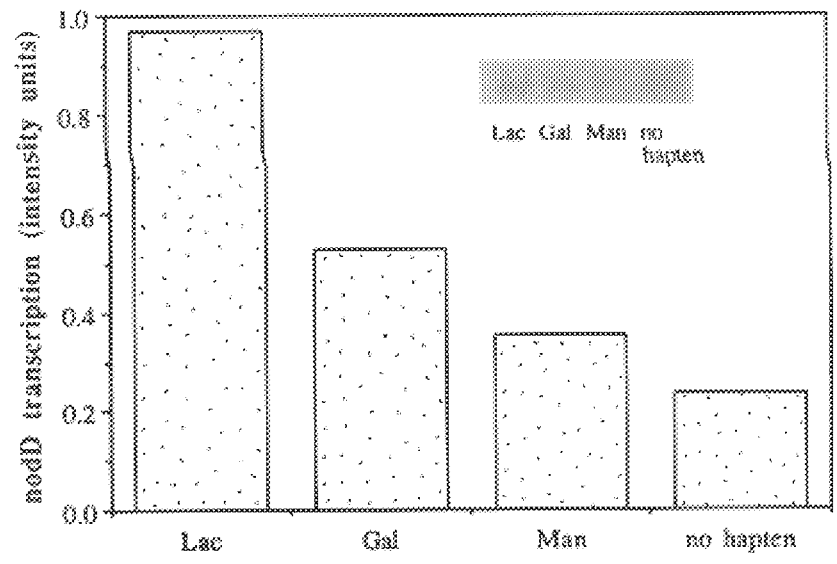

Northern blot analyses of saccharide treated samples also revealed mRNA transcripts of 1.5 kb and 2.8 kb similar to that obtained with the flavone induction (FIGS. 5A and 5B). The intensities of both of these bands were strongest in the Lac-treated cells, followed by galactose (Gal) and mannose (Man). This relative order of induction of both transcripts was similar to that reported for saccharide induction of BJ38 at the protein level (Loh, J. T., et al., Glycoconjugate J., 11:363–370 (1994)).

When the $nodD_1$ probe was used to probe the RNA samples isolated from both untreated and saccharide treated *B. japonicum* cells, a single $nodD_1$ species of ~1.6 kb was observed. Interestingly $nodD_1$ transcript levels were also found to be elevated in a saccharide dependent fashion. The order of saccharide induction was similar to that observed with BJ38 expression, with lactose yielding the greatest effect. Mannose, which had little or no effect on BJ38 expression, had only a minimal effect on $nodD_1$ transcription.

In previous publications (Loh, J. T., et al., Glycoconjugate J., 11:363–370 (1994)), it was shown that BJ38 expression at the polypeptide level could be induced by treatment of *B. japonicum* cells with either the genistein and Lac. The present invention characterizes the effect of both flavonoid compounds and saccharides on BJ38 and $nodD_1$ expression at the molecular level. The key findings of this invention are (a) the levels of BJ38 mRNA transcripts were elevated by both saccharides and flavonoids in an order of efficacy similar to that reported at the polypeptide level (Loh, J. T., et al., Glycoconjugate J., 11:363–370 (1994)); (b) $nodD_1$ induction by flavonoids demonstrated a strong correlation to that observed in the flavonoid regulation of BJ38; (c) nodd mRNA levels were also elevated in a saccharide dependent fashion. This order of induction was: Lac>Gal>Man.

A key factor in the interpretation of these results is the validity of the BJ38 probe PCR1. This probe was obtained by PCR amplification of *B. japonicum* genomic DNA using degenerate primers derived from the partial amino acid sequences of BJ38 that had been digested with V8 protease. PCR1 yielded a deduced amino acid sequence (SEQ ID NO:1) that matched the experimentally derived BJ38 amino sequence at both ends corresponding to the PCR primers, as well as in internal regions bounded by the primers. PCR1 was thus used as an authentic probe for BJ38. In genomic Southern blot analyses of *B. japonicum* DNA that had been digested with restriction enzymes that do not possess cleavage sites within the PCR1 probe, two bands were revealed. Consistent with this, two transcripts of 1.5 kb (transcript I) and 2.8 kb (transcript II) were detected in Northern blot analyses of *B. japonicum* RNA. At the present time, we do not know whether these results reflect two BJ38 genes or the presence of another gene, besides BJ38, that can hybridize to PCR1. In addition, it is also not known whether both transcript I and transcript II are derived from one or two different genes. The present results nevertheless demonstrate inducibility for both transcripts and provoke several intriguing observations. Firstly, the observation that BJ38 can be induced by flavonoid compounds such as genistein, raises the possibility that BJ38 is a member of the nod gene family. This possibility was tested by monitoring, in parallel, the levels of the $nodD_1$ transcript. $NodD_1$ was chosen as a marker for nod gene expression as it is inducible by flavonoids (Banfalvi, Z., et al., Mol. Gen. Genet. 214:420–424 (1988)), as well as codes for the trancriptional regulator of other nod genes (Gottfert, M., et al., Mol. Plant-Microbe Interact. 5:257–265 (1992)). Flavonoid induction of $nodD_1$ demonstrated a strong correlation to that observed for flavonoid regulation of BJ38. The possibility exists, therefore, that the addition of genistein to *B. japonicum* cultures results in an increased expression of the $nodD_1$ gene product, which, in turn, activates the transcription of the BJ38 gene.

Second, the observation that $nodD_1$ mRNA levels were induced by saccharides indicate alternative inducers of this gene besides the flavonoid compounds. Consistent with this, Banfalvi et al (Banfalvi, Z., et al., Mol. Gen. Genet. 214:420–424 (1988)) have reported that the induction of nod genes with soybean exudate results in induction levels of nod genes greater than that obtained with the flavonoid inducers alone. As saccharides are a major component of the soybean root exudate, the possibility exists that saccharides may provide an additional component leading to the maximal induction of $nodD_1$ expression observed with soybean root exudate. Recently, Smit et al (Smit, G., et al., J. Biol. Chem. 267:310–318 (1992)) have also reported that glycoside derivatives of flavonoid compounds are actively involved in the specific induction of the $nodD_1$ gene. The possibility of a dual control of the $nodD_1$ gene by both flavonoids and saccharides in *B. japonicum* is especially intriguing in light of studies on the regulation of the vir genes in *Agrobacterium tumefaciens* (Cangelosi, G. A., et al., Proc. Natl. Acad. Sci. USA 87:6708–6712 (1990); and Ankenbauer, R. G., et al., J. Bacteriol. 172:6442–6446 (1990)). In this connection, there is a striking analogy between the control of the nod genes of *B. japonicum* and the vir genes in *A. tumefaciens* (Table I).

TABLE I

Comparison of *A. tumefaciens* vir gene induction and *B. japonicum* nod gene induction.

| Inducer | | vir gene induction | | nod gene induction |
|---|---|---|---|---|
| | a. | saccharides: galacturonic acid > glucuronic acid > xylose > glucose | a. | saccharides: Lac > Gal > Man |
| | b. | phenolics: e.g. acetosyringone | b. | flavonoids: eg. genistein |
| carbohydrate-binding receptor | | ChvE | | BJ38 |
| sensory protein | | VirA | | NodV |
| DNA binding protein | | VirG | | NodW |
| | | | | NodD |

For instance, the *A. tumefaciens* vir genes necessary for the infection of the host plant are also activated by both saccharides and phenolics. This activation involves a two-component sensory transduction pathway composed of a sensor-kinase protein (VirA) and a DNA binding protein (VirG). Saccharide induction of the vir genes through this transduction system is mediated by the carbohydrate binding protein ChvE. When bound by its ligands, ChvE activates the sensory transduction pathway resulting in the transcription of the vir genes. The observation that the saccharide specific of $nodD_1$ induction is similar to the saccharide binding specificity of BJ38 suggests the likelihood that BJ38 serves as an analogous saccharide receptor in *B. japonicum* leading to the activation of the $nodD_1$ gene. If indeed $nodD_1$ regulation did occur via such a sensory transduction pathway, a possible candidate for both the sensor kinase and DNA binding protein components in *B. japonicum* would be the NodV and NodW proteins, respectively. These proteins are essential for the full expression for the common $nodD_1$ and nodYABCSUIJ operons and have been proposed to form an alternative pathway for nod gene induction by flavonoids (Sanjuan, J., et al., Mol. Plant-Microbe Interact. 7:364–369 (1994)). In addition, sequence analyses of NodV have also shown it to be homologous to the VirA protein (Gottfert, M., et al., Proc. Natl. Acad. Sci. USA 87:2680–2684 (1990)).

The results have demonstrated that mRNA levels of BJ38 are increased by both genistein and Lac. In this connection, there is a direct correlation between the efficacy of induction by different flavonoids on BJ38 and $nodD_1$ expression. This result suggests the possibility that BJ38 may belong to the family of nod genes required for modulation.

EXAMPLE 2

The specific objectives of the present Example are:

(i) isolation of super binding strains of *B. japonicum* which have exceptional capacity for BJ38 expression;

(ii) evaluation of the competitiveness of the super binding strains against other indigenous rhizobium strains; and (iii) enhancement of nodulation by genetic manipulation.

The isolation of binding deficient mutants after chemical mutation of wild-type *B. japonicum* R110d by negative selection based on their inability to bind to soybean SB-1 cells (Ho, S.C., et al., J. Cell Biol. 111:1631–1638 (1990)) is known. The selection of super binders in the present invention makes use of the positive selection of those bacteria that bind to soybean SB-1 cells. Based on previous experience on immuno-localization of BJ38 on *B. japonicum* cell surface by immunofluorescence, in any given population of bacteria, there is always a subpopulation of cells being unlabeled. Among the labeled cells, some showed brighter fluorescence than the others. This differential expression of BJ38 is also reflected from the binding study only certain percentage of cells are able to bind to soybean root. The need is to isolate stable bacterial strains with consistent expression of BJ38 as well as high binding activity. Two approaches are used for the selection. The first is the spontaneous mutants from the wild-type population *B. japonicum* R110d. This bacterial strain has been agronomically used throughout the United States for many years. An advantage of using this strain is that it has high nitrogen fixing activity. However, this strain is less competitive against some indigenous strains, such as *B. japonicum* 123. Second, bacteria are screened from field isolates. A moderate collection of isolates from various geographic locations throughout the United States is available. It is particularly suitable for this purpose.

*B. japonicum* R110d binding to SB-1 cells undergoes two phases of binding. An initial loose binding which can be easily removed by high salt buffer (such as PBS with 0.137 M NaCl). After 2 hours of incubation, the bacteria go through a second phase of attachment by which the bacteria remain stably bound during the high-salt washing. The number of bound bacteria continued to increase until saturation attended at about 8–10 hours. The following procedure for selection of super binder strains is performed. The bacteria are cultured to the late exponential phase of growth, at which *B. japonicum* exhibits maximum binding activity. About $10^8$ bacteria are inoculated into a SB-1 cell culture ($1\times10^6$). After 2 hours of incubation at 27° C., the cells are washed with PBS. The bacteria remained bound to SB-1 cells are plated out onto YEM agar plates. After four days of culture, the bacteria are subjected to four more cycles of selection. The bound bacteria at the end of the selection are plated out as single colonies for further testing on various phenotypes.

a) Binding kinetics of various strains of *B. laponicum*:

The bacteria are evaluated in their binding kinetics to the soybean SB-1 cells and soybean roots. Similar to the procedure as stated above for the super binding strain selection the bacteria are cultured to the late-exponential phase of growth and then incubated with the soybean SB-1 cells or roots at various time periods (0–10 h). The soybean cells/roots are washed to remove unbound bacteria. The amount of bacteria bound are quantitated by radio-immunoassay using anti-Brj antibody. In parallel, this data is confirmed by light microscopy and colony counting methods. These methods have been established (Ho, et al., J. Cell Biol. 111:1631–1638 (1990); Ho, et al., Plant J. 5:873–884 (1994)).

b) BJ38 expression

The expression of BJ38 in response to known inducers, such as lactose and genistein is compared in parallel to evaluate the level of inducibility above basal levels. Furthermore, various bacteria are tested for BJ38 inducibility in the presence of seed extracts and root exudates, which was shown to contain flavonoids important for the bacterial infection.

Expression of BJ38 is examined by immunofluorescence microscopy and by actual quantitation of the isolated BJ38 protein. For immunofluorescence microscopy, *B. japonicum* are covalently attached to the glass coverslips activated by amino propyl trimethoxy silane and glutaraldehyde (Loh, J. T., et al., Glycoconjugate J., 11:363–370 (1994). The cells are blocked in 5 BSA-PBS for 2 hours, and labeled with anti-BJ38 antisera (1:20 dilution in 5% BSA-PBS). Fluorescein isothiocyanate (FTIC)-conjugated goat anti-rabbit antibody are used as secondary antibody for visualization. Bacterial strains with intense fluorescence labeling are selected.

For isolation of BJ38, *B. japonicum* cells are cultured in the presence of 1 mM lactose or 2 $\mu$M genistein to induce BJ38 expression. After the bacteria are cultured to the late exponential phase, the bacteria will be harvested, lysed and extracted with PBS, and isolated by affinity chromatography on a Lac-Sepharose column. The isolated BJ38 are quantitated by silver stain after electrophoresis on a SDS-polyacrylamide gel using carbonic anhydrase as protein standard.

c) Nodulation and nitrogen fixation:

(i) direct inoculation: Soybean seeds (Glycine max (L.) Merr. CV. Williams) are surface sterilized and planted in the green house to allow germination for 4 days. Bacteria (with serial dilutions) are inoculated in the pots. The soybean plants are grown for 15 or 30 days after the bacterial treatment. The number of nodules, their wet weights and nitrogen fixation activity of the nodules are determined. The acetylene-reduction assay is used to determine nitrogen fixation activity (Hardy, R.W.F., et al., Soil Biol. Biochem. 5:47–81 (1973)). These parameters are tabulated and compared.

(ii) Spot inoculation: This test examines the efficiency of nodule initiation of the bacteria. The super binding strains are tested by spot inoculation method. Soybean seeds are germinated and grown in growth pouch for three days. Various bacterial strains are spot inoculated directly on the elongation zone right after the root cap, which is shown to be the zone most susceptible for modulation. The position of the root tip are marked on the outside of the growth pouch to indicate the position at the time of inoculation. The soybean plants are kept in the growth chamber to allow nodulation to develop. At the 14th day, the number and the distance of nodules from the root-tip marked at the time of inoculation are determined. The rhizobium strains that induced the highest number of nodules with the shortest distance indicate that these strains exhibit high nodulation efficiency.

d) Isolation of Nod factors and root hair deformation assays:

There are considerable evidence suggesting that the synthesis of Nod factors were induced in response to the plant signals. In soybean, the most potent inducers are genistein and daizein. These flavonoids act on the nodD protein which leads to the activation of nod gene expression. These nod genes code for enzymes responsible for the synthesis of the glycosidic backbone and the modification of the oligosaccharides. These Nod factors secreted into the rhizosphere, induce host responses, such as root hair deformation, membrane depolarization, and cortical cell division. The fact that BJ38 is also induced by genistein leads to the belief that BJ38 may belong to the nod gene family. On the other hand, lactose, a potent BJ38 inducer, also induce $NodD_1$ expression to the same extent as that induced by genistein. These results suggest that lactose may also induce nod genes, either through activation of $nodD_1$ activation or through a NodD independent pathway. Regardless of the mechanism of activation of nod genes, the end results would be the induction of Nod factor synthesis. The increase in Nod factors expression may be an important determinant in interstrain competition for nodulation.

In an attempt to quantitate the active signal molecules, the filtrate of the lactose or genistein induced culture of *B. japonicum* strains is extracted by organic solvents. Most of the root hair deformation activity is detected in the butanol-soluble fraction (Stacey, G. S., et al., J. Bacteriol. 176:620–633 (1994)). If necessary, this extract is fractionated by chromatography on a silica gel 60 column with a 60:40 acetonitrile/water gradient for elution. These eluted fractions are tested for root hair deformation.

Root hair deformation assays are analyzed on G. max CV. Essex and Glycine soja seedlings. These seeds are surface sterilized and germinated. Seedlings are transferred to sterile tubes coating 1 ml of plant nutrient solution, a filter paper strip, and serial dilutions of nod factor or crude butanol extract. Roots are examined microscopically for root hair deformations 1, 2, 3 and 4 days after inoculation. Activity of a given dilution are scored as positive when at least 50% of the seedlings showed strong root hair deformation. Alfalfa seedlings are used as negative controls for testing *B. japonicum* extract.

e) Induction of nodulation by lactose, genistein and others:

Saccharides and flavonoids induce BJ38 as well as nodD1 expression. Since lactose can induce NodD1, this raised a distinct possibility that other nod genes are also activated by lactose. This notion leads to the hypothesis that lactose by itself can promote nodulation by stimulation of BJ38 gene as well as other nod genes. Since lactose is commercially available and economical, and genistein is expensive for agricultural field application, it would be an alternative to test lactose as an inducer for modulation. Lactose is a disaccharide and many microorganisms would use this compound as a general carbon source for growth. The addition of excess lactose to the field could disturb the ecosystem, which could in turn cause deteriorating effect by stimulating growth of other pathogens. Therefore, caution must be taken to ensure optimum concentration for nod gene induction and to prevent overgrowth of pathogens. Maximum BJ38 expression in B. japonicum can be induced at a concentration of about 1 mM lactose. This concentration of lactose is also effective in inducing maximum nodD1 expression equivalent to that of which has shown to be induced by genistein. On the other hand, 1 mM lactose would not have any toxic effect on soybean plant growth as examined by histological methods. The bacteria are treated with lactose or genistein before the inoculation into the plants. This prevents complication of the system by addition of lactose directly into the soil.

Although the plant lectin, soybean agglutinin (SBA) does not appear to play a direct role in the attachment of B. japonicum (Dazzo, F. B., In Experimental Microbial Ecology. R. Burns, and T. Slater, editors. Blackwell Scientific Publications, Oxford, U.K. pp. 431–446 (1982)), it can interact with the bacterial surface. Moreover, it has been documented that SBA can enhance nodulation, either by facilitating nodule initiation at low inoculum of bacteria (Stacey, G., et al., Arch. Microbiol. 132:219–224 (1982)) or by reversing the effect of a mutant B. japonicum that exhibits a delayed nodulation (Stacey, G., et al., Arch. Microbiol. 132:219–224 (1982); Halverson, L. J., et al., Plant Physiol. 77:621–625 (1985); Halverson, L. J., et al., Appl. Environ. Microbiol. 51:753–760 (1986); Halverson, L. J., et al., Plant Physiol. 74:84–89 (1984)). Similarly, in this study, the effect of BJ38 binding on B. japonicum surface on nodulation is also tested. BJ38 can have similar stimulatory effect on nodulation.

(ii) Evaluation of the competitiveness of the super binding strains:

a) Binding assay:

Super binding B. japonicum strains can successfully compete against other Rhizobium strains. Strains superior in occupying potential nodulation site can be more competitive in nodule occupancy. The competition of the super binding strains against other Rhizobium is evaluated in soybean root.

Various ratios of the super binder and other competitive strains are inoculated onto the soybean roots. After incubation for time periods of 0.5, 1.0, 2.0 and 4.0 hours, the plant roots are washed to remove unbound bacteria. The bound bacteria are released by homogenization and plated onto agar medium for colonies to develop. Two replica are made on IMMOBULON membranes. The bacteria bound onto the membrane are screened with the respective anti-Rhizobium antiserum. The number of bound bacteria for each bacterial strain is determined and compared. For the tested strains with different serogroups, immunofluorescent technique can directly distinguish bacterial strains right on the roots. The number for each strain are counted and compared. For other bacterial strains, wherever applicable, antibiotic sensitivity, protein banding patterns, phage typing and DNA finger printing, are for strain identification.

b) Competition on nodule occupancy:

It is anticipated that better competitors for binding to the potential nodulation sites can result in better nodule occupancy. Most legumes have autoregulation mechanisms to control the number of nodules formed (Pierce, M., et al., Plant Physiol. 73:286–290 (1983); and Ride, R. W., et al., J. Plant Physiol. 122:121–137 (1986)). This autoregulation becomes critical if the low-nitrogen-fixing indigenous strains first occupy the nodulation site. In such instance, the high-nitrogen-fixing inocula have less chance of further inducing nodule formation in the host. The following experiment is to address the issue.

The super binding strains are tested initially by spot inoculation as described before. The rhizobium strains that induced the highest number of nodules with the shortest distance indicate these strains exhibit high nodulation efficiency. Competitive assay are then performed with mixed inocula, to examine the competitiveness among various strains. After the induction of nodules, the bacterial strains from each nodule are cultured in agar plates to develop individual colonies. The nodule occupancy for each strain of the bacteria is determined by serotyping with the respective antiserum by colony lift method as indicated above for antibody screening. The number of nodules, duration for nodule induction as determined by the distance from the root-tip mark is tabulated and compared. Further testing is then performed in the pot and field methods.

Figure 6:
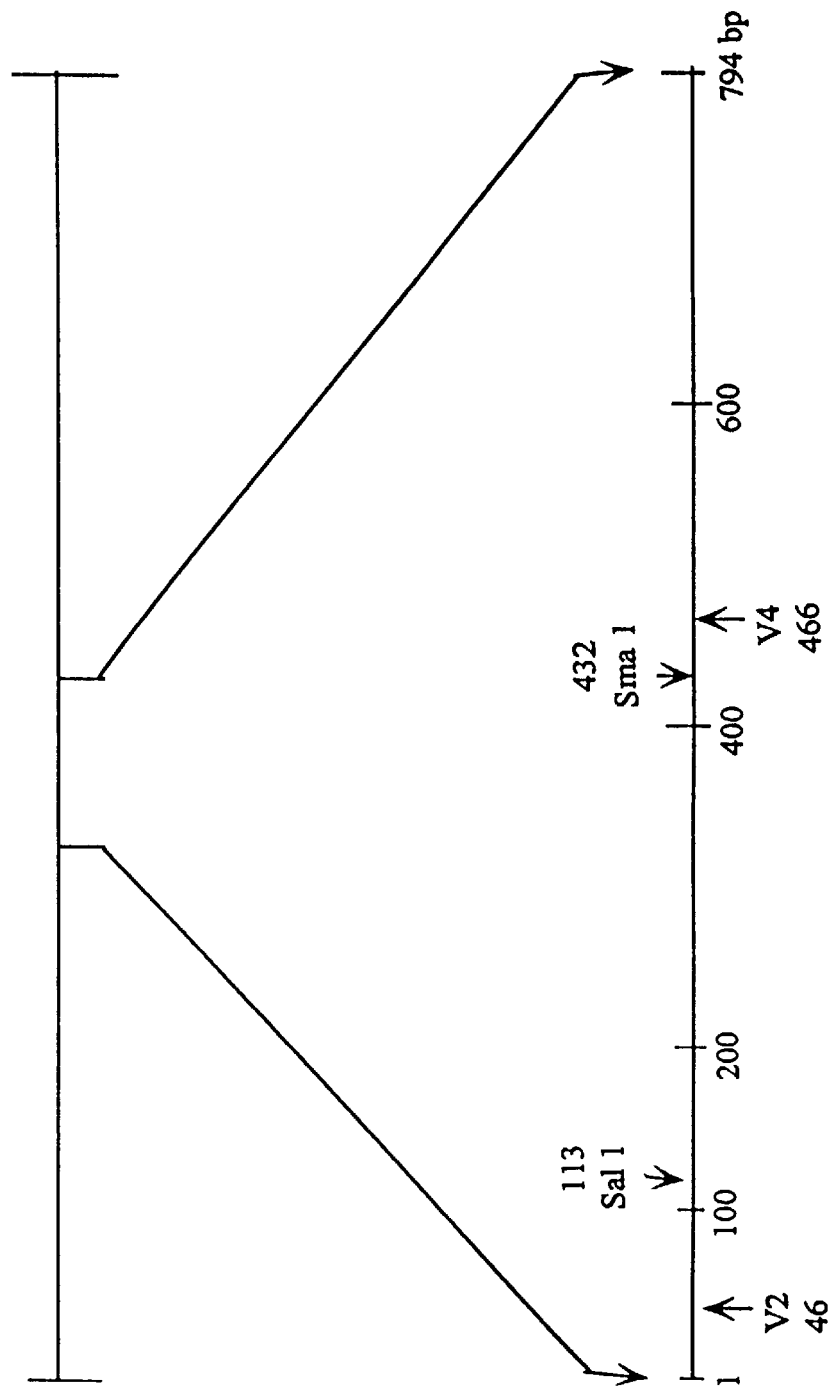

(iii) Enhancement of modulation by genetic manipulation:

SEQ ID NO:1 shows the DNA sequence of the PCR fragment of the BJ38 gene isolated as shown in FIG. 6. The sequence of 794 nucleotides in the 7 kb insert of pBS-L3R2 clone is shown in FIGS. 7A to 7C. The amino acid sequence, deduced from the nucleotide sequence, is shown below the DNA sequence. The underline below the amino acid sequence indicates those residues confirmed by the experimentally determined amino acid sequence of the BJ38 polypeptide.

With the structural gene in hand, the gene is genetically manipulated to control its levels of expression in B. japonicum. BJ38 gene is cloned into plasmids downstream of a synthetic promoter. In this way, the transcription and translation can be optimized depending on the plasmid used. T7 promoter is used for high level inducible expression in E. coli. When used in Rhizobium, this strong promoter is able to induce high level expression similar to that in the E. coli. In addition, it can also maintain low level constitutive expression in Rhizobium under non-induced condition (Spaink, H. P., et al., In New horizons in nitrogen fixation. Palacios R., Mora, J. Newton, W. E. pp 165–170 (1993)). On the other hand, increase basal level of BJ38 expression is achieved by introducing a plasmid with high copy number (Long, S. R., Cell 56:203–214 (1989)). If activation of BJ38 gene directly correlates with the $nodD_1$ other nod gene expression, the Nod factor synthesis is also activated. Therefore, infectivity is enhanced.

Similar to this strategy, when other known nod genes, such as nodABC, nodH, nodL, nodm, and nodZ, are combined with BJ38 in a high copy number DNA construct, it can have a synergistic effect on the infectivity of the bacteria.

The present invention is concerned with a major obstacle that soybean farmers face everyday, which is the indigenous poor nitrogen fixers which lower the grain yield. Normal inoculants only have about 10–45% nodule occupancy due to their poor competitiveness against the indigenous strains. If the superior strains are provided this can increase nodule occupancy by 20%. It is estimated that the soybean grain yield can be increased by 8–10%. This significant increase in production can result in an increased profit margin by the farmers.

It is intended that the foregoing description be only illustrative of the present invention and that the present invention be limited only by the hereinafter appended claims.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 794
        ( B ) TYPE: Nucleotide
        ( C ) STRANDEDNESS: Double
        ( D ) TOPOLOGY: Linear ( i i ) MOLECULE TYPE:
        ( A ) DESCRIPTION: DNA ( i i i ) HYPOTHETICAL: No ( i v ) ANTI-SENSE: No ( v ) FRAGMENT TYPE:

( v i ) ORIGINAL SOURCE:
        ( A ) ORGANISM: Bradyrhizobium japonicum
        ( B ) STRAIN:
        ( C ) INDIVIDUAL ISOLATE:
        ( D ) DEVELOPMENTAL STAGE: N/A
        ( E ) HAPLOTYPE: N/A
        ( F ) TISSUE TYPE: N/A
        ( G ) CELL TYPE: N/A
        ( H ) CELL LINE: N/A
        ( I ) ORGANELLE: N/A ( v i i ) IMMEDIATE SOURCE:

( v i i i ) POSITION IN GENOME: N/A ( i x ) FEATURE:
        ( A ) NAME/KEY: DNA encoding carbohydrate
            binding protein
        ( B ) LOCATION: chromosome DNA
        ( C ) IDENTIFICATION METHOD: sequencing
        ( D ) OTHER INFORMATION: promotes binding to
            soybean ( x ) PUBLICATION INFORMATION: N/A ( x i ) SEQUENCE DESCRIPTION: SEQ ID NO: 1:

```
GTGACAGTAG  TTTGGTTATA  GCGAGTGCTG  CCGCCTTGGT  TCCTACTGTT          50

GGAGCGCTAA  GCGCGCGTTT  CTTTATAGTG  GAACGCCTAG  CTAGAGCGCT         100

GGCTCACGGC  AGCTGGTCAA  CGACTTTCAC  CAGCTTGACG  GGCGTCAGCC         150

CAAAACCCCG  CCGCAGTACG  TCACGTACAC  CCGCAACTTG  GTGGTGGTGG         200

ATGTTCCCCC  GTCAGATATG  CAAGCTAAAC  CCAAAGTTGC  TGACCGGTGT         250

GACTGGTTGG  GCTGGTCTTG  GTTCGCCGCC  CTTTGGTCCA  AGTTGTAGCG         300

CGAACCTTAC  CGGCCAAGCG  GATGGTCTTA  ACGCAGCCAC  ACTGCTGGTT         350

GACGTTTTGG  CTTTTACCGT  GTCTATACGG  CCGCGCGAAT  TTTCGGAGTT         400
```

```
              GCTGCAAGTA  CGGGTTAGGG  CCCGAACCCT  CGTTGCGCAG  CCCTCTATGC      450

GGCGTCCTTC  ACCACAAGGA  ACAGTGGCTG  CCGCACCTCC  TGTTCTAGCA      500

GAGCCCGCGA  AGCTGAACGG  GGTTGCGCTC  GGAGCGGAGG  TTGTTAGCTA      550

CGGTCGTCGG  CGAGCTGTGC  TGCTAGACGT  GCTGGTAGTT  CTTGGCCCCG      600

TAATTCTAGC  ACAGGAGATG  TGCCTTATGA  ACGTTGAATT  CTGGGGGTTA      650

TAGGGCCAGT  GCTTGTCGAC  CATGTACGAG  ACCCACCTGG  GCATGTTGCG      700

CGGATGAAGG  AACAGGCCCT  GGTAGCGCGT  TTTTGACGTT  AGTGCAGAAG      750

CGGACCGAAG  ATACGGAGGC  AGGTTTGGCC  ACCGCTGTAA  AGGC            794
```

( 2 ) INFORMATION FOR SEQ ID NO:2:

( i ) SEQUENCE CHARACTERISTICS:
        ( A ) LENGTH: 23
        ( B ) TYPE: Nucleotide
        ( C ) STRANDEDNESS: Single
        ( D ) TOPOLOGY: Linear ( i i ) MOLECULE TYPE:
        ( A ) DESCRIPTION: Nucleotide ( i i i ) HYPOTHETICAL: No ( i v ) ANTI-SENSE: No ( v ) FRAGMENT TYPE: Synthetic primer ( v i ) ORIGINAL SOURCE:
        ( A ) ORGANISM: N/A
        ( B ) STRAIN: N/A
        ( C ) INDIVIDUAL ISOLATE: N/A
        ( D ) DEVELOPMENTAL STAGE: N/A
        ( E ) HAPLOTYPE: N/A
        ( F ) TISSUE TYPE: N/A
        ( G ) CELL TYPE: N/A
        ( H ) CELL LINE: N/A
        ( I ) ORGANELLE: N/A ( v i i ) IMMEDIATE SOURCE:

( v i i i ) POSITION IN GENOME: N/A ( i x ) FEATURE:
        ( A ) NAME/KEY: primer
        ( B ) LOCATION: N/A
        ( C ) IDENTIFICATION METHOD: sequencing
        ( D ) OTHER INFORMATION: binds nodD1 gene ( x ) PUBLICATION INFORMATION: N/A ( x i ) SEQUENCE DESCRIPTION: SEQ ID NO: 2:

```
              ATCTAAATCT  TCTCGTTGCG  CTC                                     23
```

( 2 ) INFORMATION FOR SEQ ID NO:3:

( i ) SEQUENCE CHARACTERISTICS:
        ( A ) LENGTH: 24
        ( B ) TYPE: Nucleotide
        ( C ) STRANDEDNESS: Single
        ( D ) TOPOLOGY: Linear ( i i ) MOLECULE TYPE:
        ( A ) DESCRIPTION: Nucleotide ( i i i ) HYPOTHETICAL: No ( i v ) ANTI-SENSE: No ( v ) FRAGMENT TYPE: synthetic primer ( v i ) ORIGINAL SOURCE:

(A) ORGANISM: N/A
                (B) STRAIN: N/A
                (C) INDIVIDUAL ISOLATE: N/A
                (D) DEVELOPMENTAL STAGE: N/A
                (E) HAPLOTYPE: N/A
                (F) TISSUE TYPE: N/A
                (G) CELL TYPE: N/A
                (H) CELL LINE: N/A
                (I) ORGANELLE: N/A (v i i) IMMEDIATE SOURCE: N/A (v i i i) POSITION IN GENOME: N/A (i x) FEATURE:
                (A) NAME/KEY: primer
                (B) LOCATION: N/A
                (C) IDENTIFICATION METHOD: sequencing
                (D) OTHER INFORMATION: binds to nodD1 gene (x) PUBLICATION INFORMATION: N/A (x i) SEQUENCE DESCRIPTION: SEQ ID NO: 3:

CGAGCAATAT CCGACGCATC CAGA                    24

(2) INFORMATION FOR SEQ ID NO:4:

(i) SEQUENCE CHARACTERISTICS:
                (A) LENGTH: 21
                (B) TYPE: Amino acid
                (C) STRANDEDNESS: Single
                (D) TOPOLOGY: Linear (i i) MOLECULE TYPE:
                (A) DESCRIPTION: Peptide (i i i) HYPOTHETICAL: No (i v) ANTI-SENSE: No (v) FRAGMENT TYPE: N/A (v i) ORIGINAL SOURCE:
                (A) ORGANISM: N/A
                (B) STRAIN: N/A
                (C) INDIVIDUAL ISOLATE: N/A
                (D) DEVELOPMENTAL STAGE: N/A
                (E) HAPLOTYPE: N/A
                (F) TISSUE TYPE: N/A
                (G) CELL TYPE: N/A
                (H) CELL LINE: N/A
                (I) ORGANELLE: N/A (v i i) IMMEDIATE SOURCE:

(v i i i) POSITION IN GENOME: N/A (i x) FEATURE:
                (A) NAME/KEY: partial amino acid sequence
                    of BJ38
                (B) LOCATION:
                (C) IDENTIFICATION METHOD: sequencing
                (D) OTHER INFORMATION: N/A (x) PUBLICATION INFORMATION: N/A (x i) SEQUENCE DESCRIPTION: SEQ ID NO: 4:

Thr Asn Xaa Ala Xaa Asp Gly Xaa Thr Xaa Asp Asn Leu
                            5                       10

Ala Ile Xaa Ala Gln Xaa Asn Ile
                15              20

(2) INFORMATION FOR SEQ ID NO:5:

(i) SEQUENCE CHARACTERISTICS:
                (A) LENGTH: 18
                (B) TYPE: Amino acid (C) STRANDEDNESS: Single
                (D) TOPOLOGY: Linear (ii) MOLECULE TYPE:
                (A) DESCRIPTION: Peptide (iii) HYPOTHETICAL: No (iv) ANTI-SENSE: No (v) FRAGMENT TYPE: N/A (vi) ORIGINAL SOURCE:
                (A) ORGANISM: N/A
                (B) STRAIN: N/A
                (C) INDIVIDUAL ISOLATE: N/A
                (D) DEVELOPMENTAL STAGE: N/A
                (E) HAPLOTYPE: N/A
                (F) TISSUE TYPE: N/A
                (G) CELL TYPE: N/A
                (H) CELL LINE: N/A
                (I) ORGANELLE: N/A (vii) IMMEDIATE SOURCE: N/A (viii) POSITION IN GENOME: N/A (ix) FEATURE:
                (A) NAME/KEY: Partial amino acid sequence
                    of BJ38
                (B) LOCATION: N/A
                (C) IDENTIFICATION METHOD: sequencing
                (D) OTHER INFORMATION: N/A (x) PUBLICATION INFORMATION: N/A (xi) SEQUENCE DESCRIPTION: SEQ ID NO: 5:

Val  Val  Phe  Leu  Val  Thr  Asp  Gly  Val  Gly  Asp  Lys  Ile  Val
                            5                              10

Ser  Gly  Ala  Ser
            15

(2) INFORMATION FOR SEQ ID NO:6:

(i) SEQUENCE CHARACTERISTICS:
                (A) LENGTH: 16
                (B) TYPE: Amino acid
                (C) STRANDEDNESS: Single
                (D) TOPOLOGY: Linear (ii) MOLECULE TYPE:
                (A) DESCRIPTION: Peptide (iii) HYPOTHETICAL: Yes (iv) ANTI-SENSE: No (v) FRAGMENT TYPE: N/A (vi) ORIGINAL SOURCE:
                (A) ORGANISM: N/A
                (B) STRAIN: N/A
                (C) INDIVIDUAL ISOLATE: N/A
                (D) DEVELOPMENTAL STAGE: N/A
                (E) HAPLOTYPE: N/A
                (F) TISSUE TYPE: N/A
                (G) CELL TYPE: N/A
                (H) CELL LINE: N/A
                (I) ORGANELLE: N/A (vii) IMMEDIATE SOURCE:

(viii) POSITION IN GENOME: N/A (ix) FEATURE:
                (A) NAME/KEY: deduced partial amino acid
                    sequence of BJ38 DNA
                (B) LOCATION: N/A (C) IDENTIFICATION METHOD: sequencing
(D) OTHER INFORMATION: N/A (x) PUBLICATION INFORMATION: N/A (xi) SEQUENCE DESCRIPTION: SEQ ID NO: 6:

Asp Asn Leu Ala Ile Arg Ala Gln Arg Asn Ile Thr Leu
                    5                       10

Arg Ile Asp
    15

(2) INFORMATION FOR SEQ ID NO:7:

(i) SEQUENCE CHARACTERISTICS:
    (A) LENGTH: 17
    (B) TYPE: Amino Acid
    (C) STRANDEDNESS: Single
    (D) TOPOLOGY: Linear (ii) MOLECULE TYPE:
    (A) DESCRIPTION: Peptide (iii) HYPOTHETICAL: No (iv) ANTI-SENSE: No (v) FRAGMENT TYPE: N/A (vi) ORIGINAL SOURCE: N/A
    (A) ORGANISM: N/A
    (B) STRAIN: N/A
    (C) INDIVIDUAL ISOLATE: N/A
    (D) DEVELOPMENTAL STAGE: N/A
    (E) HAPLOTYPE: N/A
    (F) TISSUE TYPE: N/A
    (G) CELL TYPE: N/A
    (H) CELL LINE: N/A
    (I) ORGANELLE: N/A (vii) IMMEDIATE SOURCE:

(viii) POSITION IN GENOME: N/A (ix) FEATURE:
    (A) NAME/KEY: deduced partial amino acid
        sequence of BJ38 DNA
    (B) LOCATION: N/A
    (C) IDENTIFICATION METHOD: N/A
    (D) OTHER INFORMATION: N/A (x) PUBLICATION INFORMATION: N/A (xi) SEQUENCE DESCRIPTION: SEQ ID NO: 7:

Thr Pro Gln Glu Val Val Phe Leu Val Thr Asp Gly Val
                    5                       10

Gly Asp Lys Ile
    15

(2) INFORMATION FOR SEQ ID NO:8:

(i) SEQUENCE CHARACTERISTICS:
    (A) LENGTH: 794
    (B) TYPE: Nucleotide
    (C) STRANDEDNESS: Double
    (D) TOPOLOGY: Linear (ii) MOLECULE TYPE:
    (A) DESCRIPTION: DNA (iii) HYPOTHETICAL: No (iv) ANTI-SENSE: No (v) FRAGMENT TYPE:

(vi) ORIGINAL SOURCE:

(A) ORGANISM: Bradyrhizobium japonicum
(B) STRAIN:
(C) INDIVIDUAL ISOLATE:
(D) DEVELOPMENTAL STAGE: N/A
(E) HAPLOTYPE: N/A
(F) TISSUE TYPE: N/A
(G) CELL TYPE: N/A
(H) CELL LINE: N/A
(I) ORGANELLE: N/A (vii) IMMEDIATE SOURCE:

(viii) POSITION IN GENOME: N/A (ix) FEATURE:
(A) NAME/KEY: DNA encoding carbohydrate binding protein
(B) LOCATION: chromosome DNA
(C) IDENTIFICATION METHOD: sequencing
(D) OTHER INFORMATION: promotes binding to soybean (x) PUBLICATION INFORMATION: N/A (xi) SEQUENCE DESCRIPTION: SEQ ID NO: 8:

| | | | | | |
|---|---|---|---|---|---|
| CACTGTCATC | AAACCAATAT | CGCTCACGAC | GGCGGAACCA | AGGATGACAA | 50 |
| CCTCGCGATT | CGCGCGCAAA | GAAATATCAC | CTTGCGGATC | GATCTCGCGA | 100 |
| CCGAGTGCCG | TCGACCAGTT | GCTGAAAGTG | GTCGAACTGC | CCGCAGTCGG | 150 |
| GTTTTGGGGC | GGCGTCATGC | AGTGCATGTG | GGCGTTGAAC | CACCACCACC | 200 |
| TACAAGGGGG | CAGTCTATAC | GTTCGATTTG | GGTTTCAACG | ACTGGCCACA | 250 |
| CTGACCAACC | CGACCAGAAC | CAAGCGGCGG | GAAACCAGGT | TCAACATCGC | 300 |
| GCTTGGAATG | GCCGGTTCGC | CTACCAGAAT | TGCGTCGGTG | TGACGACCAA | 350 |
| CTGCAAAACC | GAAAATGGCA | CAGATATGCC | GGCGCGCTTA | AAAGCCTCAA | 400 |
| CGACGTTCAT | GCCCAATCCC | GGGCTTGGGA | GCAACGCGTC | GGGAGATACG | 450 |
| CCGCAGGAAG | TGGTGTTCCT | TGTCACCGAC | GGCGTGGAGG | ACAAGATCGT | 500 |
| CTCGGGCGCT | TCGACTTGCC | CCAACGCGAG | CCTCGCCTCC | AACAATCGAT | 550 |
| GCCAGCAGCC | GCTCGACACG | ACGATCTGCA | CGACCATCAA | GAACCGGGGC | 600 |
| ATTAAGATCG | TGTCCTCTAC | ACGGAATACT | TGCAACTTAA | GACCCCCAAT | 650 |
| ATCCCGGTCA | CGAACAGCTG | GTACATGCTC | TGGGTGGACC | CGTACAACGC | 700 |
| GCCTACTTCC | TTGTCCGGGA | CCATCGCGCA | AAAACTGCAA | TCACGTCTTC | 750 |
| GCCTGGCTTC | TATGCCTCCG | TCCAAACCGG | TGGCGACATT | TCCG | 794 |

(2) INFORMATION FOR SEQ ID NO:9:

(i) SEQUENCE CHARACTERISTICS:
(A) LENGTH: 260
(B) TYPE: Amino Acid
(C) STRANDEDNESS: Double
(D) TOPOLOGY: Linear (ii) MOLECULE TYPE:
(A) DESCRIPTION: Peptide (iii) HYPOTHETICAL: No (iv) ANTI-SENSE: No (v) FRAGMENT TYPE:

(vi) ORIGINAL SOURCE:
(A) ORGANISM: Bradyrhizobium japonicum
(B) STRAIN:
(C) INDIVIDUAL ISOLATE:

(D) DEVELOPMENTAL STAGE: N/A
(E) HAPLOTYPE: N/A
(F) TISSUE TYPE: N/A
(G) CELL TYPE: N/A
(H) CELL LINE: N/A
(I) ORGANELLE: N/A (vii) IMMEDIATE SOURCE:

(viii) POSITION IN GENOME: N/A (ix) FEATURE:
(A) NAME/KEY: DNA encoding carbohydrate binding protein
(B) LOCATION: chromosome DNA
(C) IDENTIFICATION METHOD: sequencing
(D) OTHER INFORMATION: promotes binding to soybean (x) PUBLICATION INFORMATION: N/A (xi) SEQUENCE DESCRIPTION: SEQ ID NO: 9:

```
Thr Asn Ile Ala His Asp G

We claim:

1. An isolated and purified DNA encoding a carbohydrate binding protein, designated as BJ38, the DNA being present in an EcoRI and BamHI segment of chromosomal DNA of *Bradyrhizobium japonicum* and recognized by a labeled DNA binding probe for the DNA selected from the group consisting of SEO ID NOS: 1 and in a Southern assay in which the wash conditions comprise 0.1% SDS and 0.1X SSC at 42° C.

2. The DNA of claim 1 contained in a plasmid in a deposit designated as ATCC 97494 (pBS-L3R2).

3. The DNA of claim 1 derived from chromosomes in *Bradyrhizobium japonicum* in a deposit designated as ATCC 55749 (R110d).

4. A recombinant plasmid containing DNA encoding a protein, designated as BJ38, the DNA being present in an EcoRI-BamHI segment of chromosomal DNA derived from *Bradyrhizobium japonicum* and recognized by a DNA binding probe for the DNA selected from the group consisting of SEO ID NOS: 1 and 8 in a Southern assay in which the wash conditions comprise 0.1% SDS and 0.1X SSC at 42° C.

5. The DNA of claim 3 wherein the segment of DNA is contained in a plasmid in a deposit designated as ATCC 97494 (pBS-L3R2).

6. The recombinant plasmid of claim 4 derived from chromosomes in *Bradyrhizobium japonicum* in a deposit designated as ATCC 55749 (R110d).

7. A *Bradyrhizobium japonicum* containing recombinant DNA encoding a carbohydrate binding protein, designated as BJ38, the DNA being present in a EcoRI and BamHI segment of Chromisomal DNA of *Bradyrhizobium japonicum* and recognized by a DNA binding probe for the DNA selected from the group consisting of SEQ ID NOS: 1 and 8 in a Southern assay in which the wash conditions comprise 0.1% SDS and 0.2X SSC at 42° C.

8. The DNa of claim 5 wherein the DNA is contained in chromosomes in a deposit designated as ATCC 55749 (R110d).

9. The Bradyrhizobium japonicum of claim 7 wherein the DNA is contained in a plasmid in a deposit designated as ATCC 97494 (pBS-L3R2).

10. The *Bradyrhizobium japonicum* of claim 7 wherein a parent strain is isolated from soybeans.

11. A method of detecting mRNA encoding a protein, designated as BJ38, which comprises:

(a) binding the mRNA with a labeled DNA binding probe specific to the mRNA encoding the BJ38 wherein the DNA binding probe for the DNA is selected from the group consisting of SEO ID NOS: 1 and 8 in a Northern assay in which the wash conditions comprise 2X SSPE and 0.1% SDS; and (b) detecting the labeled DNA binding probe bound to the mRNA.

12. The method of claim 11 wherein the DNA is contained in a plasmid in a deposit designated as ATCC 97494 (pBSL3R2).

13. A method of detecting a segment of DNA encoding a protein, designated as BJ38, which comprises:

(a) digesting DNA of *Bradyrhizobium japonicum* with endonucleases EcoRI and BamHI to produce the segment of the DNA which encodes a RNA for the BJ38;

(b) binding the segment of the DNA of the *Bradyrhizobium japonicum* with a labeled DNA probe which selectively binds the DNA on the segment selected from the group consisting of SEO ID NOS: 1 and 8 in a Southern assay in which the wash conditions comprise 1% SDS and 0.1X SSC at 42° C.; and (c) detecting the labeled DNA probe bound to the segment of the DNA.

14. The method of claim 13 wherein the DNA for the probe is contained in a deposit designated as ATCC 97494 (pBSL3R2).

15. A method for producing a cDNA encoding a carbohydrate binding protein, designated as BJ38, which comprises:

(a) binding oligonucleotide primers selected from the group consisting of (DNA encoding) SEO ID NOS: 4, 5, 6, 7, 9 and DNA selected from the group consisting of SEO ID NOS: 1 and 8 which are unique for DNA encoding the protein with DNA from *Bradyrhizobium japonicum;*

(b) amplifying the primed DNA by means of a polymerase chain reaction (PCR) comprising a denaturation step (94° C., 2 minutes), followed by 35 amplification cycle of denaturation (94° C. 1 minute), annealing (55° C., 1 minute) and extension (72° C., 2 minutes) to produce the cDNA; and (c) isolating the cDNA.

16. The method of claim 15 wherein the oligonucleotide primers are derived from a DNA selected from the group consisting of SEQ ID NO:1 and SEO ID NO:8.

* * * * *

UNITED STATES PATENT AND TRADEMARK OFFICE
CERTIFICATE OF CORRECTION

PATENT NO. : 5,863,728

DATED : January 26, 1999

INVENTOR(S) : John Siu-Cheong Ho, John T. Loh, Melvin S. Schindler and John L. Wang It is certified that error appears in the above-identified patent and that said Letters Patent is hereby corrected as shown below:

Column 3, line 29, "nodd" should be --nodD--.

Column 3, line 38, "nodd, nodD$_1$, and noD$_2$" should be --nodD, nodD$_1$, and nodD$_2$--.

Column 3, line 40, "is of lavonoids" should be --isoflavonoids--.

Column 3, line 43, "McLouchlin" should be --McLoughlin--.

Column 4, line 31, "$^{32}$-labeled" should be --$^{32}$P-labeled--.

Column 4, line 34, "1 agarose" should be --1% agarose--.

Column 4, line 43, "nodd" should be --nodD--.

Column 7, line 33, "800 ethanol" should be --80% ethanol--.

Column 7, line 48, "0.1 Ficoll" should be --0.1% Ficoll--.

Column 8, line 25, "(glna)" should be --(glnA)--.

Column 8, line 38, "Vi(38 kd)" should be --V1(38 kd)--.

Column 9, line 9, "glna" should be --glnA--.

UNITED STATES PATENT AND TRADEMARK OFFICE
CERTIFICATE OF CORRECTION

PATENT NO. : 5,863,728

DATED : January 26, 1999

INVENTOR(S) : John Siu-Cheong Ho, John T. Loh, Melvin S. Schindler and John L. Wang It is certified that error appears in the above-identified patent and that said Letters Patent is hereby corrected as shown below:

Column 9, line 42 "(glna)" should be --(glnA)--.

Column 10, line 49 "nodd" should be --nodD--.

Column 13, line 18, "*laponicum*" should be --*japonicum*--.

Column 13, line 46, "5 BSA" should be --5% BSA--.

Column 14, line 12, "modulation" should be --nodulation--.

Column 15, line 11, "modulation" should be --nodulation--.

Column 16, line 35, "modulation" should be --nodulation--.

Column 16, line 67, "nodm" should be --nodM--.

Column 31, line 7, "SEO ID NOS: 1 and in" should be --SEQ ID NOS:1 and 8 in--.

Column 31, line 20, "SEO ID" should be --SEQ ID--.

Column 31, line 35, "0.2X SSC" should be --0.1X SSC--.

Column 32, line 2, "SEO ID" should be --SEQ ID--.

Column 32, line 18, "SEO ID" should be --SEQ ID--.

UNITED STATES PATENT AND TRADEMARK OFFICE
CERTIFICATE OF CORRECTION

PATENT NO. : 5,863,728
DATED : January 26, 1999
INVENTOR(S) : John Siu-Cheong Ho, John T. Loh, Melvin S. Schindler and John L. Wang It is certified that error appears in the above-identified patent and that said Letters Patent is hereby corrected as shown below:

Column 32, line 31, "SEO ID" should be --SEQ ID--.

Column 32, line 33, "SEO ID" should be --SEQ ID--.

Column 32, line 38, "cycle" should be --cycles--.

Column 32, line 45, "SEO ID" should be --SEQ ID--.

Signed and Sealed this

Seventeenth Day of August, 1999

Attest:

Q. TODD DICKINSON

*Attesting Officer*

*Acting Commissioner of Patents and Trademarks*